United States Patent
Hell et al.

(10) Patent No.: US 8,084,754 B2
(45) Date of Patent: Dec. 27, 2011

(54) HIGH SPATIAL RESOLUTION IMAGING OF A STRUCTURE OF INTEREST IN A SPECIMEN

(75) Inventors: Stefan Hell, Göttingen (DE); Christian Eggeling, Göttingen (DE); Alexander Egner, Göttingen (DE); Jonas Fölling, Göttingen (DE); Andreas Schönle, Göttingen (DE); Mariano Bossi, Buenos Aires (AR)

(73) Assignee: Max-Planck-Gesellschaft zur Förderung der Wissenschaften E.V., München (DE)

( * ) Notice: Subject to any disclaimer, the term of this patent is extended or adjusted under 35 U.S.C. 154(b) by 0 days.

(21) Appl. No.: 13/013,359

(22) Filed: Jan. 25, 2011

(65) Prior Publication Data
US 2011/0160083 A1 Jun. 30, 2011

Related U.S. Application Data

(60) Division of application No. 12/128,948, filed on May 29, 2008, now Pat. No. 7,880,150, which is a continuation-in-part of application No. PCT/EP2007/003714, filed on Apr. 27, 2007.

(30) Foreign Application Priority Data

May 6, 2006 (DE) .................. 10 2006 021 317

(51) Int. Cl.
*G01N 21/64* (2006.01)
(52) U.S. Cl. .................................................. 250/459.1
(58) Field of Classification Search .............. 250/459.1
See application file for complete search history.

(56) References Cited

U.S. PATENT DOCUMENTS

| | | | |
|---|---|---|---|
| 6,667,830 | B1 | 12/2003 | Iketaki |
| 7,535,012 | B2 | 5/2009 | Betzig |
| 7,586,688 | B2 | 9/2009 | Wiederhoft |
| 7,626,694 | B2 | 12/2009 | Betzig |
| 7,626,695 | B2 | 12/2009 | Betzig |
| 7,626,703 | B2 | 12/2009 | Betzig |

(Continued)

FOREIGN PATENT DOCUMENTS

EP 1 903 336 A1 3/2008
(Continued)

OTHER PUBLICATIONS

Betzig, E.: "Proposed method for molecular optical imaging", Optics Letters 1995, vol. 10, No. 3, S. 237-239 Feb. 1, 1995.

(Continued)

*Primary Examiner* — Constantine Hannaher
(74) *Attorney, Agent, or Firm* — Thomas, Kayden, Horstemeyer & Risley, LLP

(57) ABSTRACT

For imaging of a structure, the structure is marked with a substance which can be converted by a switching signal from a first into a second state, and which provides an optical measurement signal in one of its states, only. The switching signal is applied such that at least 10% of the molecules of the substance being in the measurement signal providing state are at a distance from their closest neighbors, which is greater than the spatial resolution limit of imaging the specimen onto a sensor array, which in turn is greater than an average distance between the molecules of the substance. From an intensity distribution of the measurement signal recorded with the sensor array, the position is only determined for those molecules of the substance which are at a distance from their closest neighboring molecules in the measurement signal providing state, which is greater than the spatial resolution limit.

40 Claims, 8 Drawing Sheets

U.S. PATENT DOCUMENTS

| | | | |
|---|---|---|---|
| 7,710,563 | B2 | 5/2010 | Betzig |
| 7,782,457 | B2 | 8/2010 | Betzig |
| 7,864,314 | B2 | 1/2011 | Betzig |
| 2004/0212799 | A1 | 10/2004 | Hell |
| 2006/0038993 | A1 | 2/2006 | Hell |
| 2007/0121204 | A1 | 5/2007 | Wiederhoft |
| 2008/0032414 | A1 | 2/2008 | Zhuang et al. |
| 2008/0068588 | A1 | 3/2008 | Hess |
| 2008/0068589 | A1 | 3/2008 | Hess |
| 2008/0070322 | A1 | 3/2008 | Hess |
| 2008/0070323 | A1 | 3/2008 | Hess |
| 2008/0076142 | A1 | 3/2008 | Knebel et al. |
| 2008/0111086 | A1 | 5/2008 | Betzig |
| 2009/0134342 | A1 | 5/2009 | Hell et al. |
| 2009/0206251 | A1 | 8/2009 | Hess |
| 2009/0279086 | A1 | 11/2009 | Hell |
| 2010/0181497 | A1 | 7/2010 | Hess |
| 2010/0181535 | A1 | 7/2010 | Tinnefeld et al. |
| 2011/0102787 | A1 | 5/2011 | Hess |

FOREIGN PATENT DOCUMENTS

| | | | |
|---|---|---|---|
| WO | 2004/090617 | A1 | 10/2004 |
| WO | 2006/127692 | A2 | 11/2006 |
| WO | 2007/030835 | A2 | 3/2007 |
| WO | 2008/074429 | A1 | 6/2008 |
| WO | 2008-080032 | A2 | 7/2008 |
| WO | 2009/003948 | A2 | 1/2009 |

OTHER PUBLICATIONS

Ram, S., et al.: "Beyond Rayleigh's criterion: A resolution measure with application to single-molecule microscopy", PNAS 2006, vol. 103, No. 12, S. 4457-4462, Mar. 21, 2006.

Geisler, C., et al.: "Resolution of λ/10rin fluorescence microscopy using fast single molecule photo-switching,", App. Phys. A 88, Jun. 2007, pp. 223-226, Jun. 1, 2007.

S. Bretschneider, et al., "Breaking the Diffraction Barrier in Fluorescence Microscopy by Optical Shelving," Phys. Rv. Lett, 98, pp. 218103-1 to 218103-4 (2007).

Shroff, H., Galbraith, C. G., Galbraith, J. A. & Betzig, E., "Live-cell photoactibated localization microscopy of nanoscale adhesion dynamics," Nat. Methods 5, 417-423 (2008).

Rust, et al., Sub-Diffraction-Limit Imaging by Stochastic Optical Reconstruction Microscopy (STORM), Nature Methods, vol. 3, No. 10, Oct. 2006, pp. 793-795.

PCT International preliminary Report and Written Opinion of co-pending related application No. PCT/EO07/003714 dated Dec. 10, 2008.

Yildiz, Ahmet, et al., "Myosin V Walks Hand-Over-hand: Single Fluorophore Imaging with 1.5-nm Localization", Science, vol. 300, pp. 2061-2065, Jun. 27, 2003.

Fölling, J.; Bossi, M.; Bock, H. et al., "Fluorescence nanoscopy by ground-state depletion and single-molecule return", Nat. Meth. vol. 5, No. 11, Nov. 2008, p. 943-945.

Heilemann, M.; van de Linde S.; Schüttpelz, M. et al., "Subdiffraction-Resolution Fluorescence Imaging with Conventional Fluorescent Probes," Angew. Chem. Int. Ed., vol. 47, 2008, p. 6172-6176.

van de Linde, S.; Schüttpelz, M.; Kasper, R. et al., "Photoswitching microscopy with subdiffraction-resolution," Proc. of SPIE: Single Molecule Spectroscopy and Imaging II. edited by J. Enderlein et al., vol. 7185, 2009, p. 71850F-1 through -11.

Betzig, E.; Patterson, G. H.; Sougrat, R. et al., "Imaging Intracellular Fluorescent Proteins at Nanometer Resolution," SCIENCE, vol. 313, Sep. 2006, p. 1642-1645.

Lidke, K. A.; Rieger, B.; Jovin, T. M.; Heintzmann, R., "Superresolution by localization of quantum dots using blinking statistics," Opt. Express, vol. 13, No. 18, Sep. 2005, p. 7052-7062.

Bates, M.; Blosser, T. R.; Zhuang, X., "Short-Range Spectroscopic Ruler Based on a Single-Molecule Optical Switch," Phys. Rev. Lett., vol. 94, 2005, p. 108101-1 through -4.

Enninga, J.; Sansonetti, P.; Tournebize, R., "Roundtrip explorations of bacterial infection: from single cells to the entire host and back," TRENDS in Microbiol., vol. 15, No. 11, 2007, p. 483-490.

Gordon, M. P.; Ha, T.; Selvin, P. R., "Single-molecule high-resolution imaging with photobleaching," Proc. Natl. Acad. Sc., vol. 101, No. 17, 2004, p. 6462-6465.

Chudakov, D. M.; Verkhusha, V. V.; Staroverov, D. B. et al., "Photoswitchable cyan fluorescent protein for protein tracking," Nat. Biotechn., vol. 22, No. 11, Nov. 2004, p. 1435-1439.

Qu, X.; Wu, D.; Mets, L.; Scherer, N. F., "Nanometer-localized multiple single-molecule fluorescence microscopy," Proc. Natl. Acad. Sc., vol. 101, No. 31, Aug. 2004, p. 11298-11303.

"Nano-Organized Polyelectrolyte Shells—Coating for Living Cells and Tissues", BioForum Europe 6, 51-59 (2005).

Hell, S. W. & Wichmann, J., "Breaking the diffraction resolution limit by stimulated emissions: stimulated-emission-depletion fluorescence microscopy," Opt. Lett. 19, 780-782 (1994).

Hell, S. W. & Kroug, M., "Ground-state-depletion fluorescence microscopy: a concept for breaking the diffraction resolution limit," Appl. Phys. B 60, 495-497 (1995).

Heintzmann, R., Jovin, T. M. & Cremer, C. J., "Saturated patterned excitation microscopy—a concept for optical resolution improvement," Opt. Soc. Am. A 19, 1599-1609 (2002).

Gustafsson, M. G. L., "Nonlinear structured-illumination microscopy: Wide-field fluorescence imaging with theoretically unlimited resolution," Proc. Nat. Acad. Sci. USA 102, 13081-13086 (2005).

Hell, S. W., Jakobs, S. & Kastrup, L., "Imaging and writing at the nanoscale with focused visible light through saturable optical transitions," Appl. Phys. A 77, 859-860 (2003).

Hell, S. W., "Far-Field Optical Nanoscopy," Science 316, 1153-1158 (2007).

Bock, H. et al., "Two-color-far-field fluorescence nanoscopy based on photoswitchable emitters," Appl. Phys. B 88 (2007), pp. 161-165.

Zondervan, R.; Kulzer, F., Orlinskii, S. B. & Orrit, M., "Photoblinking of Rhodamine 6G in Poly(vinyl alcohol): Radical Dark State Formed through the Triplet," J. Phys. Chem. A 107, 6770-6776 (2003).

Bossi, M. et al., "Multicolor Far-Field Fluorescence Nanoscopy through Isolated Detection of Disinct Molecular Species," Nano Lett. 8, 2463-2468 (2008).

Dickson, R. M., Cubitt, A. B., Tsien, R. Y. & Moerner, W. E., "On-off blinking and switching behaviour of single molecules of green fluorescent protein," Nature 388, 355-358 (1997).

Reindl, S. & Penzkofer, A., "Higher excited-state triplet-singlet intersystem crossing of some organic dyes," Chem. Phys. 211, 431-439 (1996).

Ringemann, C. et al., "Enhancing Fluorescence Brightness: Effect of Reverse Intersystem Crossing Studied by Fluorescence Fluctuation Spectroscopy," ChemPhysChem, 612-624 (2008).

Eggeling, C., Widengren, J., Rigler, R. & Seidel, C. A. M., "Photobleaching of Fluorescent Dyes under Conditions Used for Single-Molecule Detection: Evidence of Two-Step Photolysis," Anal. Chem. 70, 2651-2659 (1998).

Donnert, G., Eggeling, C. & Hell, S. W., "Major signal increase in fluorescence microscopy through dark-state relaxation," Nat. Methods 4, 81-86 (2007).

Boyarskiy, V. P. et al., "Photostable, Amino Reactive and Water-Soluble Fluorescent Labels Based on Sulfonated Rhodamine with a Rigidized Xanthene Fragment," Chem. Eur. J. 14, 1784-1792 (2008).

Westermann, B. & Neupert, W., "Mitochondria-targeted green fluorescent proteins: convenient tools for the study of organelle biogenesis in *Saccharomyces*," Yeast 16, 1421-1427 (2000).

Griesbeck, O., Baird, G. S., Campbell, R. E., Zacharias, D. A. & Tsien, R. Y., "Reducing the Environmental Sensititivyt of Yellow Fluorescent Protein," J. Biol. Chem. 276, 29188-29194 (2001).

Lamesch, P. et al., "hORFeome v3.1: A resource of human open reading frames representing over 10,000 human genes," Genomics 89, 307-315 (2007).

Qu, Xioaohui, et al., Nanometer-localized Multiple Single-Molecule Fluorescence Microscopy, PNAS, vol. 101, No. 31, Aug. 3, 2004, pp. 11298-11303.

Kural, Comert, et al., "Kinesin and Dynein Move a Peroxisome in Vivo: A Tug-of-War or Coordinated Movements?", Science, vol. 308, Jun. 3, 2005, pp. 1469-1472.

HIGH SPATIAL RESOLUTION IMAGING OF A STRUCTURE OF INTEREST IN A SPECIMEN

CROSS-REFERENCE TO RELATED APPLICATIONS

This application is a divisional of U.S. utility patent application Ser. No. 12/128,948 entitled "High Spatial Resolution Imaging of a Structure of Interest in a Specimen", which was filed on 29 May 2008 now U.S. Pat. No. 7,880,150 as a continuation in part of International Patent Application PCT/EP2007/003714 entitled "Method and Fluorescent Light Microscope for the High-Resolution Three-Dimensional Representation of the Structure of a Specimen", which was filed on 27 Apr. 2007 and claims the priority of German Patent Application No. DE 10 2006 021 317.3 entitled "Verfahren and Fluoreszenzlichtmikroskop zum räumlich hochauflösenden Abbilden einer Struktur einer Probe" [Method and fluorescent light microscope for the high spatial resolution imaging of a structure of a specimen], which was filed on 6 May 2006 and which led to German Patent DE 10 2006 021 317.3 of 11 Oct. 2007.

FIELD OF THE INVENTION

The invention relates to a method for the high spatial resolution imaging of a structure of interest in a specimen. More precisely, the invention relates to a method for high spatial resolution imaging of a structure of interest in a specimen, having the steps of: selecting a substance from a group of substances which can be converted by a switching signal; marking the specimen's structure of interest with molecules of the substance; applying an intensity of the switching signal to the specimen; imaging the specimen onto a sensor array; using the sensor array to register an optical signal which comes from the substance in order to record a distribution of the signal over the sensor array.

BACKGROUND OF THE INVENTION

A method for the high spatial resolution imaging of a structure of interest in a specimen with the steps specified above, which is referred to as RESOLFT (REversible SaturabIe OpticaL Fluorescence Transition), is known from US 2004/0212799 A1 and US 2006/0038993 A1. Here, when converting the substance into the second state by the switching signal, only a defined spatial region of the specimen is respectively omitted deliberately. This region is an intensity minimum of an interference pattern with a zero position, and the intensity of the switching signal is already so large everywhere in the vicinity of the zero position that it exceeds a saturation threshold for complete switching of the substance into the second state. In this way an optical measurement signal, which comes from the fraction of the substance remaining in the first state, can be assigned to the specimen's region deliberately omitted by the switching signal. The spatial resolution for imaging the specimen's structure of interest, which is marked with the substance, therefore no longer depends on the spatial resolution limit of the imaging of the specimen onto the sensor array being used. Rather the spatial resolution is defined by the extent of the zero position of the switching signal, within which the substance still lies in the first state, since there is no measurement signal which can come from the vicinity of the zero position and accordingly needs to be assigned to a spatial position separable from the position of zero position. When spatially imaging the structure of interest in a specimen, it is therefore possible to go below the resolution limit (i.e. the Abbe limit due to diffraction, which is given by the wavelength of the light divided by two times the numerical aperture) which in principle restricts the spatial resolution of the imaging optical methods and depends directly on the wavelength of the longest-wave relevant optical signal.

The substances used in the above-described RESOLFT method for marking the structure of interest in the specimen are switchable fluorescent dyes. This is explained in US 2004/0212799 A1 and US 2006/0038993 A1 in that they are selected from a group of substances which can be converted repeatedly by a switching signal from a first state having first optical properties into a second state having second optical properties, and which can return from the second state into the first state, the two states differing at least in respect of one of the following criteria: conformational state of a molecule; structural formula of a molecule; spatial arrangement of atoms within a molecule; spatial arrangement of bonds within a molecule; accumulation of further atoms or molecules on a molecule; grouping of atoms and/or molecules; spatial orientation of a molecule; mutual orientation of neighboring molecules and ordering formed by a multiplicity of molecules and/or atoms.

The placement of the zero position of the switching signal within the specimen can be determined from the intensity distribution of the measurement signal over the sensor array with an accuracy higher than the spatial resolution limit of the imaging, if it is certain that the measurement signal comes only from the region of this one zero position. Besides the size of the zero position, the accuracy achievable in the location determination essentially depends only on the density of the pixels of the sensor array, which is conventionally a CCD or CMOS camera, as well as the signal-to-noise ratio achieved and the width of the point spread function of the imaging. Specifically, the accuracy achievable for the location determination is even much finer than the spacing of the pixels of the sensor array divided by the imaging scale; with a good signal-to-noise ratio even much less than one nanometer, which is known to the person skilled in the art.

It is also known to use this phenomenon for the localization of individual fluorescent molecules in a specimen. A prerequisite for this, however, is that the individual fluorescent molecules lie at a distance from their respective closest neighboring molecules which is greater than the spatial resolution limit of the imaging of the specimen onto the sensor array, since otherwise the optical measurement signals received by the sensor array from the individual fluorescent molecules merge together. When this happens, the positions of the individual molecules can no longer readily be determined.

In the method known from US 2004/0212799 A1 and US 2006/0038993 A1 and all previous methods in which a structure of interest in a specimen is marked with a substance emitting a measurement signal, i.e. in particular a fluorescent substance, the density of the molecules of the substance in the specimen is regularly so large that the distance of the individual molecules from their closest neighbors corresponds only to a small fraction of the spatial resolution limit of the specimen's imaging onto the sensor array.

WO 2006/127692 A2 has disclosed a method for the high spatial resolution imaging of a structure of interest in a specimen, in which the structure of interest is marked with switchable fluorescent dyes in the form of so-called phototransportable optical markings. A subgroup of the markings is respectively activated into a state in which they can be excited to emit fluorescent light. The respective subgroup comprises so few of the markings that they lie at a distance from one another which is greater than the spatial resolution limit for imaging the specimen onto the sensor array. This makes it possible, after exciting the markings of the subgroup into fluorescence, to localize the origin positions of the fluorescent light with a resolution better than the diffraction limit which applies for the spatial resolution for imaging the specimen onto the sensor array, so that a point of the marked structure of interest is also respectively recorded with this increased resolution. The phototransformable optical markings are defined in WO 2006/127692 in that they can be switched on by an activating signal into a state in which they can be excited to emit fluorescent light. This activating signal may be the same as the excitation light which subsequently excites the markings into fluorescence. More specific embodiments of phototransformable optical markings, which are disclosed in WO 2006/127692, comprise exclusively a photoactivatable fluorescent proteins, i.e. molecules which become a fluorophore only after they have absorbed at least one light quantum, or in other words they initially need to be switched on before they are fluorescent. The activating or switching process entails a modification of the molecular structure of the molecules (relocation of atom groups or even breaking or forming a bond). The method known from WO 2006/127692 is also referred to as PALM (Photoactivated Localization Microscopy).

A similar method known as STORM (Stochastic Optical Reconstruction Microscopy) and described by Rust et al. in Nature Methods, 3, 793-796 (2006) likewise uses molecules switchable into a fluorescent state, i.e. switchable fluorescent dyes, although these are not proteins but photoswitchable organic fluorophores, specifically the fluorescent dyes Cy3 and Cy5. It is known of these cyanine dyes that they can be switched between different conformational states, more specifically isomeric states.

A disadvantage of the PLM and Storm methods is that it is not possible in them to predict when the structure of interest in the specimen will be recorded so fully that determining the position of further molecules provides no additional useful information and the method may therefore be terminated.

The range of switchable proteins and fluorophores, which may be used for the RESOLFT, PALM and STORM methods explained above, is very small compared with the total number of fundamentally known and available fluorescent dyes. Dyes which are both switchable and (in one of the switching states) capable of fluorescence, are very rare. They are therefore synthesized and optimized by elaborate methods. Added to this, the switching behavior and the fluorescent behavior depend very strongly on the chemical environment of the molecule. This applies both for switchable fluorescent proteins and for switchable organic fluorophores. This deficiency is to be regarded as fundamental, and it is associated inter alia with the fact that fluorescence and switching of the molecule are mutually competitive molecular processes which often compete with one another from the same excited state. The brightness of the switchable fluorescent dyes in their fluorescent state, i.e. the relative yield of fluorescent light from a molecule during repeated excitation, is also often only small compared with a multiplicity of nonswitchable organic fluorophores and nonswitchable fluorescent proteins. The strong restrictions due to switchable proteins or fluorophores, however, have to date being tolerated in order to obtain the high spatial resolutions achievable by the aforementioned methods for imaging structures of interest.

In so-called GSD (Ground State Depletion) microscopy (S. Bretschneider et al.: Breaking the diffraction barrier in fluorescence microscopy by optical shelving, Phys. Rev. Lett. 98, 218103 (2007)), the diffraction limit for imaging a structure marked by a fluorescent dye in a specimen is overcome by converting the respective fluorescent dye outside the respective measurement point from its electronic ground state, from which it can be excited into fluorescence by excitation light, into a dark electronic state in which it is not capable of fluorescence. This is done before exciting the remaining molecules at the measurement point into fluorescence by depopulating light with the same wavelength as the excitation light. The dark electronic state is typically a triplet state, while the ground state of the fluorescent dye is a singlet state. The molecules typically return thermally, i.e. not (optically) switched, from this dark state into the electronic ground state, so that only light of a single wavelength i.e. the excitation light is necessary for carrying out the experiment.

SUMMARY OF THE INVENTION

A first aspect of the present invention provides a method for high spatial resolution imaging of a structure of interest in a specimen, having the steps: selecting a substance from a group of substances which can be converted repeatedly by a switching signal from a first state into a second state, which can return from the second state into the first state, and which provide an optical measurement signal in one of their first and second states only; marking the specimen's structure of interest in the specimen with molecules of the substance; applying an intensity of the switching signal to the specimen in order to convert fractions of the substance into the second state by the switching signal, the intensity of the switching signal being set such that at least 10% of the molecules of the substance being in the one of the first and second states providing the optical measurement signal are at a distance from their closest neighboring molecules in the one of the first and second states providing the optical measurement signal, which is greater than the spatial resolution limit of the imaging of the specimen onto the sensor array; imaging the specimen onto a sensor array, a spatial resolution limit of the imaging being greater than an average distance between closest neighboring molecules of the substance in the specimen; using the sensor array to register the optical measurement signal which comes from the specimen, in order to record an intensity distribution of the measurement signal over the sensor array; separating the optical measurement signal which comes from molecules of the substance in the one of the first and second states providing the optical measurement signal, which are at a smaller distance from one another than the distance which is greater than the spatial resolution limit of the imaging of the specimen onto the sensor array, from the optical measurement signal which comes from the molecules of the substance in the one of the first and second states providing the optical measurement signal, which are at a distance from their closest neighboring molecules in the one of the first and second states providing the optical measurement signal, which is greater than the spatial resolution limit of the imaging of the specimen onto the sensor array; and determining the position in the specimen of the molecules of the substance from the intensity distribution of the measurement signal over the sensor array coming from the molecules of the substance in the one of the first and second states providing the optical measurement signal, which are at a distance from their closest neighboring molecules in the one of the first and second states providing the optical measurement signal, which is greater than the spatial resolution limit of the imaging of the specimen onto the sensor array, only.

A second aspect of the present invention provides a method for high spatial resolution imaging of a structure of interest in a specimen, having the steps: selecting a substance from a group of substances, which have a first state with first fluorescent properties and a second state with second fluorescent properties; which can be excited by light of one wavelength to spontaneously emit fluorescent light; which can be converted from the first state into their second state by the light of the one wavelength and which can return from their second state into their first state; marking the specimen's structure of interest with molecules of the substance; imaging the specimen onto a sensor array, a spatial resolution limit of the imaging being greater than an average spacing between closest neighboring molecules of the substance in the specimen; exposing the specimen to the light of the one wavelength in a region which has dimensions larger than the spatial resolution limit of the imaging of the specimen onto the sensor array, at such an intensity that fractions of the molecules of the substance are being excited by the light of the one wavelength to spontaneously emit fluorescent light and being converted into their second state, and that at least 10% of the molecules of the substance belonging to the fraction of the molecules of the substance being excited by the light of the one wavelength to spontaneously emit fluorescent light are at a distance from their closest neighboring molecules belonging to the fraction of the molecules of the substance being excited by the light of the one wavelength to spontaneously emit fluorescent light, which is greater than the spatial resolution limit of the imaging of the specimen onto the sensor array; registering the fluorescent light which is spontaneously emitted out of the region by varying fractions of the molecules of the substance being excited by the light of the one wavelength to spontaneously emit fluorescent light, in a plurality of images recorded by the sensor array during continued exposure of the region to the light of the one wavelength; and separating the fluorescent light which comes from molecules of the substance being excited by the light of the one wavelength to spontaneously emit fluorescent light, which are at a smaller distance from one another than the distance which is greater than the spatial resolution limit of the imaging of the specimen onto the sensor array, from the optical measurement signal which comes from the molecules of the substance being excited by the light of the one wavelength to spontaneously emit fluorescent light, which are at a distance from their closest neighboring molecules being excited by the light of the one wavelength to spontaneously emit fluorescent light, which is greater than the spatial resolution limit of the imaging of the specimen onto the sensor array; and determining the position in the specimen of the molecules of the substance from the fluorescent light recorded by the sensor array coming from the molecules of the substance being excited by the light of the one wavelength to spontaneously emit fluorescent light, which are at a distance from their closest neighboring molecules being excited by the light of the one wavelength to spontaneously emit fluorescent light, which is greater than the spatial resolution limit of the imaging of the specimen onto the sensor array, only.

The two aspects of the present invention have substantial identical overlaps, even though they will sometimes be explained in more detail separately below.

When converting the fraction of the substance into the second state in the method of the first aspect of the present invention, an intensity of the switching signal is set so that a substantial percentage of the molecules respectively remaining in the first state lie at a distance from their closest neighboring molecules in the first state which is greater than the spatial resolution limit of the imaging of the specimen onto the sensor array. For each molecule of the substance which belongs to this substantial percentage, its position in the specimen can be determined from the intensity distribution over the sensor array of the optical measurement signal coming from it, with the already fundamentally known extremely high position resolution which considerably surpasses the spatial resolution limit of the imaging of the specimen onto the sensor array. This moreover also allows the specimen's structure of interest, marked with the substance, to be imaged with this extremely high position resolution. It is then only necessary for other molecules of the substance to be reset into the first state, these molecules belonging to the substantial percentage of the molecules of the substance in the first state in which they lie at a distance from their closest neighboring molecules in the first state which is greater than the spatial resolution limit of the imaging of the specimen onto the sensor array. This represents no problem, however, that since the selection of the molecules for which this condition applies is based on transition probabilities and therefore obeys statistical laws. Since statistically speaking, other molecules of the substance will tend to be switched into the second state, the specimen's structure marked with the substance will be interrogated with ever-higher density according to the position of the individual molecules of the substance. The sum of these positions is the image of the structure of interest, obtained by the new method, which has the position resolution far finer than the conventional resolution limit. Admittedly, individual molecules may repeatedly belong to the selection which satisfies the criterion applied here. Yet precisely when only a comparatively small fraction of the molecules present overall in the specimen's region in question is converted into the second state and fulfils the distance criterion, the fraction of molecules whose exact location may be determined repeatedly is negligible compared with the fraction of molecules which belong only once to the substantial percentage for which accurate determination of the location is possible, even with frequent repetition of the conversion of the fraction of the substance into the second state. Even if this fraction is larger, at worst the efficiency is thereby impaired, i.e. in particular the speed but not the function of the new method. This is due to the fact that by selecting the molecules for the position determination with maximal position resolution based on transition probabilities, given a sufficiently high number i.e. a sufficiently large random sample range, owing to statistical laws the ensemble of molecules whose positions are determined is representative of the ensemble of molecules of the substance which are present in the specimen and therefore the specimen's structure of interest marked with them.

In order to be able to determine the placement of the molecule in the specimen from the intensity distribution over the sensor array of the measurement signal coming from a molecule of the substance in the first state, with a position resolution higher than the spatial resolution limit of the imaging of the specimen onto the sensor array, it is to be understood that the grid dimension of the pixels of the sensor array must at least be smaller than the spatial resolution limit times the imaging factor of the imaging. The greater dimensioning is preferably only at most half as great as the spatial resolution limit times the imaging factor of the imaging, so that the measurement signal coming from a molecule is distributed over at least four pixels of the sensor array. A much smaller grid dimension of the pixels of the sensor array is not associated with a corresponding increase in the position resolution when determining the placement of the molecules in the specimen. Rather, it entails the risk that the signal-to-noise ratio will become significantly worse. A grid dimension which lies between 60 and 10% of the spatial resolution limit times the imaging factor of the imaging will therefore generally be most favorable.

The substantial percentage of the molecules respectively remaining in the first state at a given time, which satisfies the criterion of the spacing of the molecules in the second state being larger than the spatial resolution of the imaging of the specimen onto the sensor array, is at least 10%. In particular when the percentage complementary thereto of the molecules in the first state which lie at a smaller distance from one another is comparatively large, it is important that the measurement signal coming therefrom or its intensity distribution over the sensor array to be separated from the measurement signal which comes from the molecules at a sufficient distance from one another. This may be done by checking whether the total intensity of the measurement signal, the shape and/or the area of the intensity distribution of the measurement signal over the sensor array corresponds to a single molecule or a plurality of molecules. Only in the event of correspondence with a single molecule is the location of this molecule then determined from the intensity distribution. It is to be understood that it is expedient to be able to determine locations of individual molecules of the substance, and therefore positions of the specimen's structure of interest, for a maximally large percentage fraction of the registered local intensity distributions. For this reason, it is preferable for a maximally large percentage of the molecules respectively converted into the second state to lie at the requisite large distance from neighboring molecules in the second state. It makes little sense, however, to attempt to prevent all the molecules actually remaining in the first state from having any neighbors which are likewise in the first state and whose spacing is less than the spatial resolution limit of the imaging of the specimen onto the sensor array, because the average spacing of the molecules which can respectively be in the second state would thereby become very large, the effect of which would be that the number of locations of molecules which can be determined after a switching process decreases again. The switching signal intensity with which the specimen's structure of interest can in the end be imaged most rapidly, i.e. with the fewest repetitions of the switching process, finally depends on how difficult it is to distinguish between intensity distributions of the measurement signal over the sensor array which are assignable to only one molecule in the first state or to two or more neighboring molecules in the first state.

Since the new method makes do without spatial structuring of the switching signal in the region of the specimen, the switching signal may in principle also be a non-optical signal, although an optical switching signal is actually preferable owing to its simpler handleability. With an optical switching signal, for example, different intensities of the switching signal may readily be applied to different regions of the specimen in order to accommodate the fact that the substance, with which the specimen's structure of interest is marked, is present in very different concentrations in these various regions. Nevertheless, it will always be the case that the intensity of the switching signal in the new method has a constant value over regions that have dimensions larger than the spatial resolution limit of the imaging of the specimen onto the sensor array. Specifically, this constant value may be set inversely proportionally to an average local concentration of the substance in this region of the specimen.

In order to establish rapidly whether the measurement signal coming from a region of the specimen, which corresponds to a plurality of pixels of the sensor array, is assignable to one or more molecules of the substance, so that it is viable to record an intensity distribution of the measurement signal in order to carry out a position determination of an individual molecule therefrom, or not, this region may be imaged in parallel with the sensor array onto a photodetector by which the chronological sequence of the emission of individual photons from the region can be observed. If only a single molecule in the region is in the first state, the photons of the measurement signal which are emitted by it will have a minimum time spacing because the molecule can respectively emit only one photon in a cycle of its excitation. Correspondingly, photons following one another more closely indicate that they have been emitted by a plurality of molecules in the region which are in the second state. In this case, the process of recording the intensity distribution of the measurement signal may be terminated and a new attempt may be made to obtain only a single molecule of the substance in the first state in the region. The photodetector for observing the chronological sequence of the emission of individual photons from the region may comprise a single detector unit, if the dead time after registering a first photon is sufficiently short. Otherwise, the photodetector should be constructed from two detector units with which a deliberate search is made for photons emitted quasi-simultaneously from the region in the scope of a coincidence detector. These are an indication of a plurality of molecules of the substance in the region simultaneously being in the second state.

As already indicated in the preceding description of the invention, it relates in particular to those embodiments of the new method with which the substance is selected from a subgroup of substances which in a first state can be excited by an optical excitation signal to spontaneously emit fluorescent light, which is registered as an optical measurement signal by the sensor array.

The substance may furthermore be selected from a subgroup of substances which can be converted from the second state back into the first state by an optical switchback signal. In this case, before converting another fraction of the substance into the second state by the switching signal, the fraction of the substance previously converted into the second state may deliberately be converted back into the first state by the switchback signal. It is not therefore necessary to wait for the time taken by the molecules of the substance to return from the second state into the first state, for example owing to thermal excitation or under the effect of the optical excitation signal, which is primarily intended here for the spontaneous emission of fluorescent light. If the half-life of the molecules of the substance in the second state has a favorable order of magnitude, however, then the new method may also be carried out very effectively when the substance is not convertible from the second state back into the first state by an optical switchback signal.

A particularly preferred group of substances for use in the new method are so-called Förster resonance energy transfer pairs, conventionally referred to as FRET pairs for short, which consist of an (energy) donor and an (energy) acceptor. Primarily those FRET pairs in which the acceptor is photochromic and is switched by the switching signal, in order to modulate fluorescence properties of the donor, are suitable for use in the new method. The acceptor itself may be fluorescent, although this will generally not be utilized in the new method.

In cases in which the structure of interest in the specimen is defined by a protein, it is advantageous for the substance, with which the structure of interest is marked, to be incorporated into the molecule or attached to it by gene technology. The incorporation or attachment may be carried out directly, i.e. the marking substance per se may be inserted into the protein in the specimen or appended to it in the scope of a fusion protein. It is however also possible merely for a binding site for the marking substance, via which the marking with the substance can then take place subsequently, to be inserted into the protein or appended to it. Such a widely known binding site for fluorescent proteins for marking a protein consists, for example, of the sequence of 4 cysteines in the amino acid sequence of the protein, i.e. a so-called tetracysteine motif. It is particularly advantageous for the gene-technological incorporation or attachment of the substance, or the binding site for the substance, into or onto the protein in the specimen to be carried out by expression of the protein modified in this way instead of the original protein in at least one cell within the specimen, so that the structure of interest is formed directly by the protein modified with the marking substance or with the binding sites for it.

The extremely high position resolution for location determination offers the opportunity to observe the spatial arrangement of very small structures in the specimen. Such a structure may consist of a single protein molecule, which is then to be marked with the substance at a plurality of different points. These points very typically lie at a distance from one another which is less than the spatial resolution limit of any conceivable optical imaging of the protein. In the new method, the measurement signal of the substance is respectively interrogated at a given time at only one of the points where the protein molecule is marked with the substance. With each repetition of the interrogation, the substance is switched over by the switching signal at only one of the marking points into the second state which delivers the measurement signal. This may admittedly be the same point as before. Yet since this process is controlled by transition probabilities, with a sufficiently large number of repetitions of the interrogation it may reliably be assumed that the substance has been interrogated at all marking points of the protein molecule and that the position of all marked points of the protein molecule has therefore been determined with a maximal position resolution. The position resolution is in this case so large that even protein foldings and other conformational changes of protein molecules become observable.

The total time required for imaging the structure of interest in a specimen can be shortened by carrying out the new method in parallel with at least two different substances, from which distinguishable optical measurement signals come in their respective first state. The speed of the new method is limited by the fact that the density of the molecules of the substance in the first state which lie at a sufficient distance from one another, and therefore the number of molecules whose locations can be determined in a cycle of the new method, is naturally restricted. So long as the optical measurement signals of two different substances marking the structure of interest differ so that they can be mutually separated, by using such different substances the number of molecules whose locations can be determined in a cycle of the new method can be increased proportionally to the number of different substances.

A specific embodiment of the method of the first aspect of the present invention, known as PALMIRA (PALM with Independently Running Acquisition), is described in C. Geisler, A. Schönle, C. von Middendorff, H. Bock, C. Eggeling, A. Egner and S. W. Hell: Resolution of/10 in fluorescence microscopy using fast single molecule photo-switching, Appl. Phys. A 88, 223-226 (2007), the disclosure of this publication being fully incorporated herein by reference. In this embodiment of the method according to the invention, a structure of interest in a specimen is marked with a switchable fluorescent protein. Specifically this is a protein by the name of rsFastLime, which by a light with a wavelength of 488 nm is not only excited into fluorescence in its initial state but also fractionally switched off into a nonfluorescent state and partially switched back again therefrom into its fluorescent state. The underlying mechanism is a conformational change of the fluorophore. These properties of the switchable fluorescent protein make it possible, with the light of only a single wavelength, alternately to set up subgroups of fluoresceable molecules of the protein in which the fluoresceable molecules lie at a mutual spacing greater than the diffraction limit, and to excite the fluoresceable molecules into fluorescence. It is thereby possible continuously, i.e. with a high frequency, for images to be recorded which register the alternating subgroups of the fluorescent molecules and in which the position of the respectively registered molecule can be determined with an accuracy beyond the diffraction limit. With the sum of the images, the structure in the specimen is recorded with a spatial resolution finer than the diffraction limit.

At the start of the exposure of the specimen to the light of the one wavelength in the method of the second aspect of the present invention, its intensity is set so that the substance is converted from its fluorescent first state into its nonfluorescent or at least distinguishably fluorescent second state until at least 10%, preferably at least 50%, more preferably at least 90% and most preferably at least 95% of the molecules of the substance which remain in the first state lie at the critical distance from their closest neighboring molecules in the first state, which is greater than the spatial resolution limit of the imaging of the specimen onto the sensor array. This is generally equivalent to saying that more than 90%, preferably more than 95%, even more preferably more than 98% and most preferably more than 99% of the molecules of the substance are converted into the second electronic state. Images, in which the fluorescent light spontaneously emitted by the substance is registered, are subsequently recorded by the sensor array while the specimen continues to be exposed to the light of the one wavelength. The effect of the intensity of the light being reduced if need be relative to the initial intensity, is that the molecules which are respectively still in the first state are excited into spontaneous emission of fluorescent light which is registered in the images, and to a smaller part are converted into the nonfluorescent or differently fluorescent first state. This smaller portion of the molecules of the substance is ideally precisely as large as a fraction of the molecules of the substance which simultaneously return from the second state into the first state spontaneously or under the effect of the same light of the one wavelength. The images recorded continuously with the exposure of the specimen to the light of the one wavelength thus always register fluorescent light from as many isolated molecules of the substance as can have their position determined in the specimen with an accuracy finer than the diffraction limit. From the sum of the individual positions registered in this way, the structure in the specimen which is marked with the substance can likewise be recorded with a spatial resolution finer than the diffraction limit.

It is not always necessary to reduce the intensity of the light of the one wavelength for recording the images; rather, this is necessary only when the initial concentration of the fluorophores was very great. For medium and low concentrations, the intensity can be adjusted from the start so that the isolation and registering of the molecules can be carried out with the same value of the intensity. This is related to the fact that the number of photons which are emitted successively as fluorescent light by the fluorescent dye in the first state until conversion into the second state (in the same fluorescence burst) is substantially independent of the intensity of the light being used.

It is extremely surprising that even though it has essentially the same procedure as the method described as PALMIRA, the method of the second aspect of the invention makes do without switchable proteins or fluorophores. Instead, as a fluorescent dye in the new method, a substance may be used in which the first and second states are different electronic states of the substance, i.e. states of the substance which differ from one another only in electronic terms. The substance then does not fall within the definitions of the substance used for the marking in US 2004/0212799 A1 and US 2006/0038993 A1, and it may be any conventional non-switchable fluorescent dye. Besides their electronic ground state from which they can be excited into fluorescence, practically all conventional fluorescent dyes have an electronic dark state into which they can be converted at a relevant rate owing to excitation with light of the same wavelength as can be used to excite the fluorescence. These are generally a singlet state as the fluoresceable ground state and a triplet state as the dark state. In normal fluorescent light microscopy, the fractional conversion of a fluorescent dye into its nonfluorescent triplet state instead of its excited singlet state—especially with high intensities of the excitation light—is known as a disadvantage because it reduces the yield of fluorescent light from a specimen. In the present invention, this effect is specifically utilized because the position of any individual molecule of the substance, with which the structure of interest in the specimen is marked, be recorded with a resolution better than the diffraction limit only when the fluorescent light from the molecule can be registered in isolation, i.e. separately from the fluorescent light of neighboring molecules. To this end, only few of the molecules should respectively be in the first state.

In the new method of the second aspect of the present invention, it is frequently advantageous to implement measures which modify the lifetime of the nonfluorescent second state of the fluorescent dye in the specimen. In contrast to conventional fluorescence microscopy, however, this often involves not shortening but extending the lifetime of the nonfluorescent second state. The measures which cause such shortening of the lifetime include cooling the specimen to low temperatures at which thermal excitations are reduced to collision-induced transitions, reducing the concentration in the specimen of oxygen which quenches the triplet state of the fluorescent dye, for example with a glucose oxidase which binds oxygen or by measurements in a vacuum, or fixing or embedding the specimen in polymers, for example PVA. The increased lifetime of the nonfluorescent second state makes it possible to keep large fractions of the fluorescent dye in the nonfluorescent second state even with lower intensities of the light of the first wavelength.

The known risk of photobleaching a conventional fluorescent dye from its triplet state likewise represents no problem in the new method. Strictly speaking, it is sufficient for a substantial fraction of the molecules of the fluorescent dye to return once into their fluorescent first state after they have been pumped into their nonfluorescent second state or differently fluorescent second state. After this return, the molecules are registered individually. Their subsequent fate is insignificant. For instance, they may enter the triplet state again and be photobleached therefrom.

Partial photobleaching of the fluorescent dye may even be carried out deliberately in the new method of the second aspect of the present invention, before the remaining unbleached molecules are registered. The new method can be carried out particularly advantageously when the molecules of the fluorescent dye do not exceed a particular spatial density in the specimen, because then a particular percentage of the molecules which remains in the first state likewise does not exceed a particular spatial density, which is essential for being able to register the individual molecules separately. If the actual concentration of the fluorescent dye in the specimen exceeds the particular spatial density, on the other hand, it may be difficult to register the molecules individually. In order to avoid this difficulty, the excess fluorescent dye may be switched off by photobleaching by means of a high intensity of the light of the one wavelength or another wavelength, i.e. converted into a persistent dark state which differs from the first state and the second state. The persistent dark state, in which the fluorescent dye is no longer involved in the steps of recording the images for registering the individual molecules, typically differs not only electronically but for example also chemically from the first state and the second state which are used according to the invention for this registering of the individual molecules.

The new method of the second aspect of the present invention was carried out successfully with commercially available fluorescent dyes known as non-switchable to any person skilled in the art, such as Rhodamine 6G. Compared with conventional fluorescent light microscopy using this fluorescent dye—apart from different preferred details in the specimen preparation—in order to be carried out the intensity of the light of the one wavelength merely needs to be tuned with the frequency at which the images are recorded by the sensor array. The equipment requirements necessary for this are available in many fluorescent light microscopes. Here, it is only necessary to modify the control of the intensity of the light of the one wavelength according to the method according to the invention. As an alternative, the frequency of the image recording by the sensor array or the camera comprising the sensor array is altered. Accordingly, the new fluorescent light microscope is distinguished only by a special design of the control for the intensity of the light of the one wavelength. Preferably, online image processing is in this case provided for the individual images recorded by the sensor array.

This evaluation is expedient in order to adjust the intensity of the light of the one wavelength to such a value which actually makes it possible to register fluorescent light of individual molecules, spatially separated from one another, in the individual images. The values set for the intensity of the light of the one wavelength may be a constant value. This also includes a very fast pulse sequence with a frequency very much higher than the image frequency of the recorded images. The intensity of the light of the one wavelength may however also have an intensity profile temporally modulated with the sequence of the recording of the images, for example in order to deliberately set up the subgroup of the molecules of the substance which are in the first state, between the individual images, and to excite primarily the molecules of the set up subgroup into fluorescence during the recording of the individual images. Furthermore, the light of the one wavelength may in this case be directed on to the respective region of interest in the continuously (with the time-modulated intensity profile) or in pulses which are not resolved in the recording of the images (likewise with the time-modulated intensity profile).

The online evaluation of the individual recorded images may be used to determine the spatially inseparable fluorescent molecules of the substance, whereupon the intensity of the light may be varied until a density threshold for such inseparable fluorescent molecules is fallen below. In this way, an upper limit for the intensity of the light of the one wavelength is defined. A lower limit may be defined in that the individual recorded images can be evaluated online with respect to the maximal density with which they show separable fluorescent molecules of the substance, and in that the intensity of the light of the one wavelength is varied until a density threshold for such separable fluorescent molecules is reached from below. While on the one hand it is important for the molecules in the fluorescent state not to have a concentration so high that they can no longer be registered separately from one another, their concentration below this limit should be as high as possible so as to obtain as much information as possible about the structure of interest with each image.

The initial exposure of the substance to the light of the one wavelength, which is primarily used to convert them essentially into their second state, may also be used to record an intensity distribution of the fluorescent light of all the substance in the specimen by the sensor array. This intensity corresponds to a concentration distribution of the substance in the specimen with the spatial resolution of the imaging of the specimen onto the sensor array.

This concentration distribution of the substance in the specimen represents an overview of the position of the structure of interest marked with the substance in the specimen. This simplifies the further steps of the new method, since it can thus for example be concentrated on to those regions of the specimen in which parts of the marked structure are actually present. This is usually not possible with switchable and above all activatable fluorophores since they are initially for the most part not in the fluorescent state, which prohibits an overview owing to the lack of signal.

Depending on the concentration distribution of the substance in the specimen, the intensity of the light of the one wavelength may also be adjusted for the region respectively to be examined in more detail, or at least it may be preset to an approximately suitable value for the fine adjustment. Furthermore, a local termination criterion for the recording of further images of the same region of the specimen may be defined on the basis of the concentration distribution of the substance in the specimen. The information content of additional images of a region of the specimen comprises a decreasing information content, the decrease in the information content depending on the concentration of the substance in the respective region. If only very few molecules of the substance are present in a region, then relatively few images are sufficient in order to record the position of a high percentage of the molecules. Further images contribute only redundant information in this regard. The situation is different with a very high concentration of the substance in a region. Here, only smaller fractions of the substance in the specimen are recorded even with many images, and each further image makes new information available.

Specifically, in the new method, each position of a molecule as registered in the successive images is entered not only into a high resolution overall image of the structure of interest in the specimen but, convoluted with the PSF (Point Spread Function) of the imaging of the specimen onto the sensor array, also into a reconstruction of the initially recorded intensity distribution. When this reconstruction has approximated the initially recorded intensity distribution to within a particular degree, no significant further information about the structure of interest is to be expected with the positions of further molecules from further images. For the convolution with the PSF, the brightness of the respective molecule may be taken into account as a weighting factor. Various values may be adopted as a measure of the similarity of the reconstruction to the initially recorded intensity distribution, for example a cross correlation, a simple difference or quadratic deviation of the normalized intensity distributions or deviations between the spatial frequencies (Fourier transforms) of the intensity distributions.

The new method is particularly well suited for marking the specimen's structure of interest with the non-switchable fluorophores by modifying a biological specimen with gene technology so that it itself expresses the non-switchable fluorescent dyes or specific binding sites for the non-switchable fluorescent dyes or for linkers coupled thereto. The structure of interest in the specimen is particularly advantageously marked in this way with non-switchable organic dyes via so-called small labels or self-labeling protein tags such as FlAsh, snap tags or halo tags. These and similar concepts are fundamentally known to the person skilled in the art, see for example BioForum Europe 6, 51-59 (2005). This makes it possible to image proteins in a biological specimen with high resolution using widespread conventional fluorescent dyes.

For the fluorescent dye which is employed in the new method, it is not crucial for its second electronic state to be nonfluorescent, i.e. not capable of fluorescent and therefore entirely dark. It may also be differently fluorescent than the first electronic state. If the fluorescent dye is in this case excited into fluorescence in the second state by the same light as in its first electronic state, it is important that the fluorescent light which is emitted by the fluorescent dye in its first electronic state can be distinguished from the fluorescent light which is emitted by the fluorescent dye in the second electronic state.

It is to be understood that the new method may be combined with various measures which are familiar to the person skilled in the art, in particular from the field of methods known as PALM and STORM. These comprise in particular measures for three-dimensional resolution of the registered positions of the molecules in the specimen, i.e. for spatial resolution of these positions in the z direction as well. These measures include multi-photon excitation of the fluorescent dye from its first state, both for fluorescence and for transition into its nonfluorescent second state by focusing the exciting light of the one wavelength onto the respective plane of interest, and using two mutually opposing objectives with high numerical aperture in 4-pi configuration for exposing the specimen to the light of the one wavelength and/or for registering the fluorescent light from the specimen. In so far as the light is then respectively focused only into one or more individual points of the plane, the plane with these points is to be scanned in all steps of the method, for example during the recording of each individual image. The focusing of the light of the one wavelength into individual points of the specimen may advantageously be combined with confocal registering of the fluorescent light from the specimen. As an alternative the specimen may be exposed, orthogonally to the direction of the imaging of the specimen onto the sensor array, to the light of the one wavelength from which a light section is formed by a cylindrical lens. This procedure is known to the person skilled in the art as SPIM (Selective Plane IlluMination).

A fluorescent light microscope for carrying out the new method differs from known fluorescence microscopes, with which a spatial resolution better than the diffraction limit is achieved, by the fact that there are no measures for finely structuring the switching signal from the switching signal source; rather, a control of the switching signal source adjusts an intensity of the switching signal according to the new method instead.

At least one photodetector may additionally be provided, onto which a region of the specimen that corresponds to a plurality of pixels of the sensor array is imaged, in order to observe the chronological sequence of the emission of individual photons from this region. As already explained in connection with the new method, with such a photodetector it is possible to establish very rapidly, i.e. in particular even before the readout of the sensor array, whether the intensity of the measurement signal of only one or more molecules of the substance is registered in the respective region, for example in order to terminate the registering in favor of a new attempt if it is not found that the intensity comes from only a single molecule. This is very important in so far as the readout of a sensor array is often the rate-limiting factor for concluding a cycle of the new method. The sensor array must be read out before the switching signal can be used to make a new selection of molecules of the substance, which are then in the state delivering the measurement signal, so that the measurement signal can come from this new selection of molecules. Sensor arrays suitable for carrying out the new method and the new fluorescent light microscope comprise CCD and preferably CMOS sensor arrays of conventional design, although when choosing these, besides the possibility of fast readout, it is necessary to ensure that the dark noise and readout noise are small enough to obtain a good signal-to-noise ratio when carrying out the new method.

A fluorescence microscope for carrying out the new method of the first aspect may furthermore comprise a separate switchback signal source for applying a switchback signal to the specimen. It has however already be indicated in the description of the new method that the substance, with which these specimen's structure of interest is marked, may also return from its second state to its first state spontaneously, i.e. by thermal excitation, or that this transition may also be triggered by the excitation signal with which the substance is primarily excited to emit the measurement signal.

BRIEF DESCRIPTION OF THE FIGURES

The invention will be understood better with reference to the following drawings. The parts in the drawings are not necessarily represented true to scale; rather, emphasis is placed on it clearly illustrating the principles of the present invention. In the drawings, references which are the same denote the same parts in the various views.

FIG. 17 (B) is a reconstruction which corresponds to a resolution-limited image of the same object as in FIG. 17 (A). The reconstruction was generated by the sum of the 61440 individual images. The small image at the bottom right in (B) shows a profile at the marked positions of FIGS. 17 (A) and (B), with the aid of which the resolution increase of the novel method may be seen clearly.

DETAILED DESCRIPTION

Figure 1:
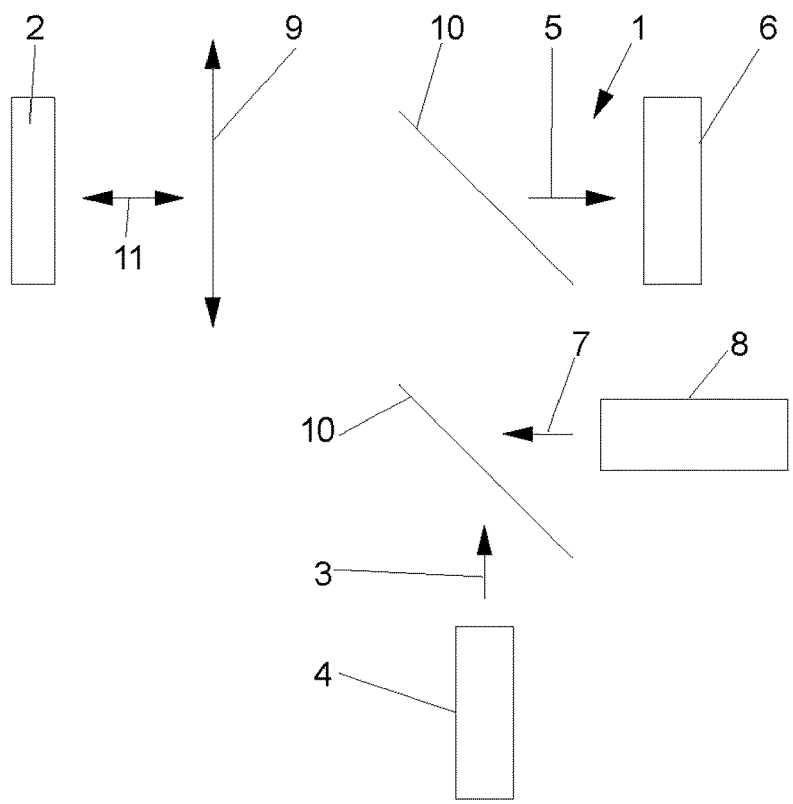
FIG. 1 schematically represents the structure of a fluorescent light microscope for the high spatial resolution imaging of a structure of interest in a specimen.

Now referring in more detail to the drawings, the fluorescent light microscope 1 schematically represented in FIG. 1 is used for the high spatial resolution imaging of a structure of interest inside a specimen 2. The structure of interest inside the specimen 2, which is not represented explicitly here, is marked with a substance whose molecules have two states, specifically a first in which they are not fluorescent and a second, in which they are excited by an optical excitation signal 3 from an excitation signal source 4 to spontaneously emit fluorescent light which is registered as a measurement signal 5 by a sensor array 6. The molecules of the substance can be switched between the first and second states by an optical switching signal 7 from a switching signal source 8. A control (not shown separately here) of the switching source 8 is configured in such a way that it adjusts the intensity of the switching signal 7 so that the number of molecules of the substance, with which the structure of interest in the specimen 2 is marked, which are in the second state is only such that the spacing of the fluorescent molecules in the second state is greater than a spatial resolution limit in the imaging of the specimen 2 onto the sensor array 6 by imaging optics 9 (only indicated in FIG. 1). This makes it possible to determine the locations of the molecules of the substance in the specimen 2 which are in the second state, based on their associated intensity distributions of the measurement signal 5 over the sensor array 6, with an accuracy which far exceeds the spatial resolution limit of the imaging and depends, besides the size of the molecules of the substance, essentially on the density of the pixels of the sensor array 6, the imaging scale and the signalto-noise ratio. The position determination may even be finer than the pixel spacing of the sensor array 6. The semitransparent mirror 10 (again only indicated in FIG. 1) is used to superimpose the beam paths of the excitation signal 3 and of the switching signal 7, or to isolate the measurement signal 5 which comes from the specimen. Narrowband color filters are generally also used here so that only the measurement signal of interest 5 and no fractions of the excitation signal 3 or the switching signal 7, reflected by the specimen, can be registered by the sensor array 6. A double arrow 11 in front of the specimen 2 indicates that the specimen 2 both is exposed to optical signals 3, 7 and emits the optical measurement signal 5.

Figure 2:
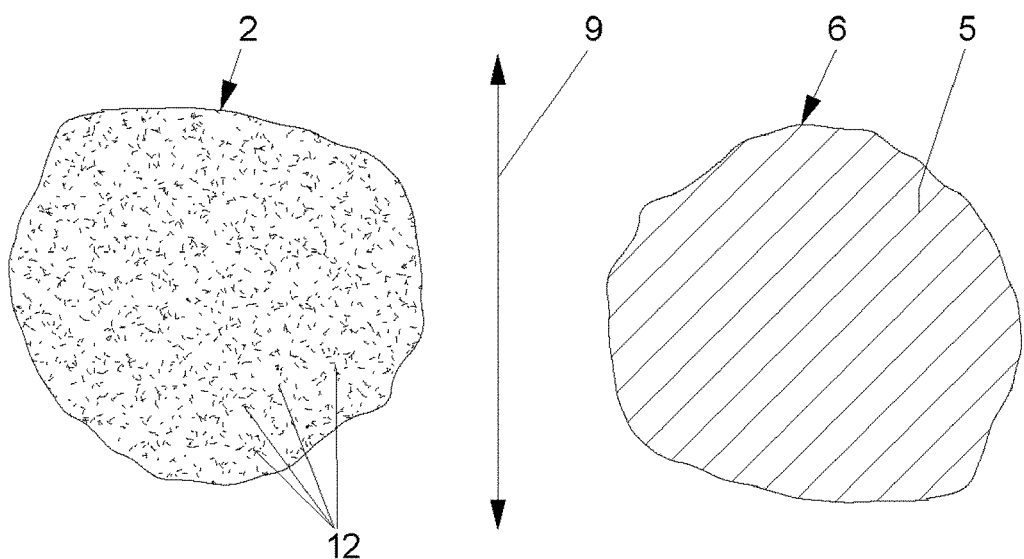
FIG. 2 schematically represents a dense uniform distribution of fluorescent molecules of a substance marking the specimen's structure of interest and the resulting intensity distribution of the fluorescent light over the corresponding region of a sensor array, onto which the specimen is imaged with the fluorescent light microscope according to FIG. 1.

FIG. 2 schematically represents a uniform statistical distribution of molecules 12 of the marking substance in the specimen 2. All of the molecules 12 represented are in their fluorescent second state. The spacing of the molecules 12 is less than the spatial resolution limit in the imaging of the specimen 2 by the imaging optics 9 onto the sensor array 6. Specifically, the spacing of the molecules 12 here is actually much less than the resolution limit. This results in an intensity distribution of the measurement signal 5 over the sensor array 6 which is constant apart from statistical fluctuations and noise, as is symbolized in FIG. 2 by uniform shading of the represented region of the sensor array 6. It is thus not possible to determine the location of individual molecules 12 from the measurement signal 5 registered by the sensor array 6. Structuring (not present in FIG. 2) of the distribution of the molecules 12 inside the specimen 2 also could only be resolved up to the spatial resolution limit of the imaging of the specimen 2 by the imaging optics 9 onto the sensor array 6 with such closely spaced molecules 12 in the fluorescent state. In the new method, in which only a small fraction of the molecules 12 is ever converted into their fluoresceable state, the density of the molecules actually present is irrelevant.

Figure 3:
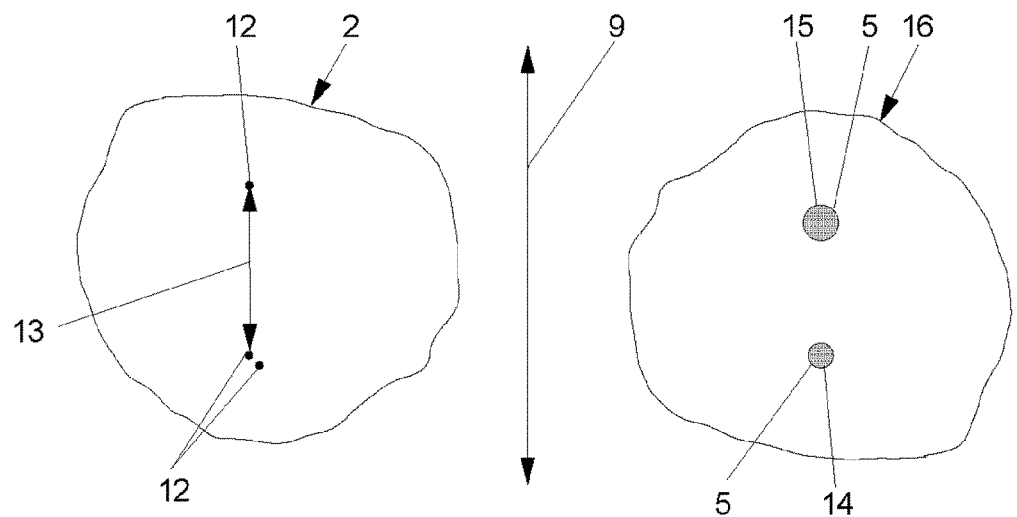
FIG. 3 schematically represents the intensity distribution of the measurement signal over the sensor array for the case of a single molecule and two closely neighboring molecules in a region of the specimen.

FIG. 3 schematically represents the imaging onto the sensor array 6 of a region of the specimen 2, in which there are in total three molecules 12 in the fluorescent second state. Two of the molecules 12 lie pairwise close together, while the distance 13 of the second molecule 12 from this pair is greater, and specifically greater than the spatial resolution limit in the imaging of the specimen 2 of the imaging optics 9 onto the sensor array 6. The spacing of the two molecules 12 of the pair, on the other hand, is smaller than the resolution limit. The sensor array 6 registers the fluorescent light coming from the molecules 12 as two discrete intensity distributions 14 and 15. The intensity distribution 14 corresponds to the single molecule 12, while the intensity distribution 15 corresponds to the pair of molecules 12.

Figure 4:
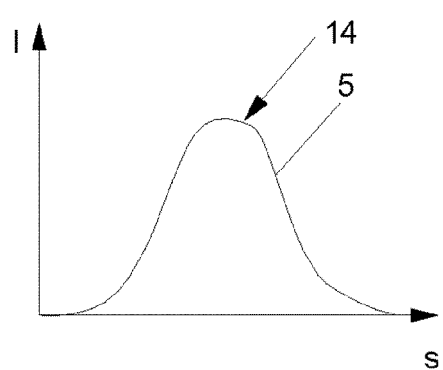
FIG. 4 is a section through the intensity distribution over the sensor array according to FIG. 3, which corresponds to one molecule.
Figure 5:
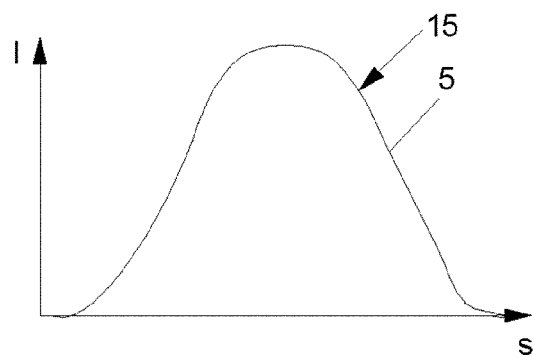
FIG. 5 is a section through the intensity distribution over the sensor array according to FIG. 3, which corresponds to the two closely neighboring molecules.

Sections through the intensity distributions 14 and 15 are depicted in FIGS. 4 and 5. The intensity distributions essentially do not differ in their shape. Both intensity distributions are in principle Airy disks. The intensity distribution 15, however, has twice as great an integral as the intensity distribution 14 and a greater width at half maximum. The location of the molecule 12 in the specimen 2 can be determined very accurately from the intensity distribution 14, specifically in particular with a resolution higher than the spatial resolution limit of the imaging of the specimen 2 by the imaging optics 9 onto the sensor array 6. The position in the x-y plane of the specimen 2 can be deduced from the lateral placement of the intensity distribution on the sensor array 6, while the shape of the intensity distribution 14 allows inferences about the location in the Z direction inside the specimen 2. The situation is different with the intensity distribution 15. A position in the specimen can admittedly also be assigned to it. This, however, is only the middle position of the two molecules 12 of the pair. The intensity distribution 15 does not reveal where the two molecules 12 are located relative to the middle position. For this reason, in the new method for the high spatial resolution imaging of a structure marked with the substance in the specimen 2, the fraction of the molecules 12 which is respectively switched by the switching signal 7 according to FIG. 1 into the fluorescent second state is only so small that as many of the molecules 12 as possible are isolated, i.e. lie at a spacing from neighboring molecules 12 so great that when imaged onto the sensor array 6 they result in a discrete intensity distribution 14 from which the location of the molecule 12 can respectively be determined exactly.

Figure 6:
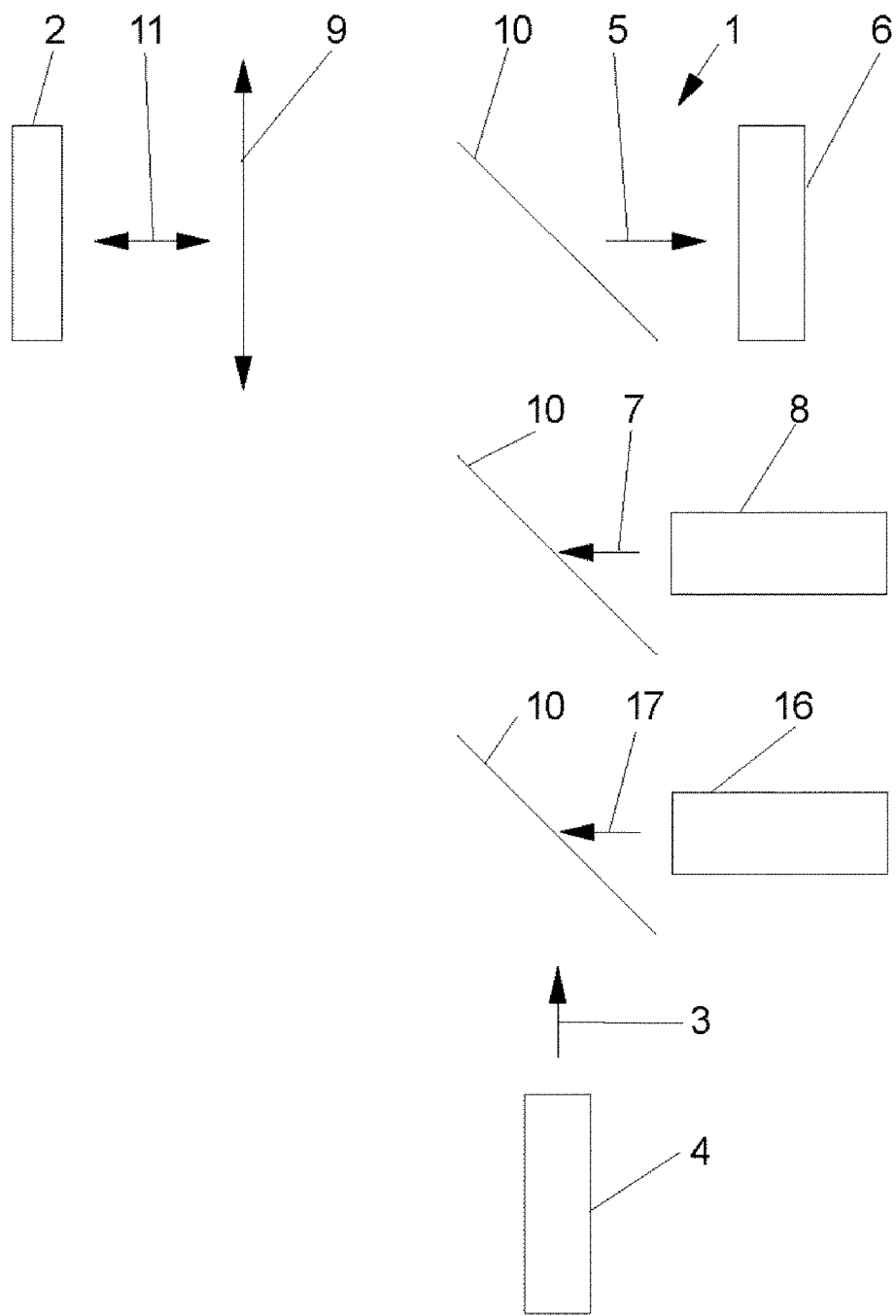
FIG. 6 schematically represents the structure of a light microscope in a second embodiment, supplemented relative to FIG. 1 by a switchback signal source.

FIG. 6 schematically represents an embodiment of the fluorescent light microscope 1 which is supplemented relative to the embodiment according to FIG. 1 by a switchback signal source 16 for applying a switchback signal 17 to the specimen 2. A further semitransparent mirror 10 is provided in order to superimpose the beam path of the optical switchback signal 17. The molecules of the substance in the specimen 2 are deliberately brought from their second state back into their first state by the switchback signal 17, in order to make a new selection of molecules with the switching signal 7 for the next round of determining the location of individual molecules in the specimen 2. In order to determine the location of enough molecules to achieve representative imaging of the structure marked with them in the specimen 2, the new method requires frequent repetition of the selection of individual molecules with the switching signal 7, with the underlying transition probabilities ensuring ever-changing selections even if individual molecules are selected several times. The switchback signal 17 is not categorically required when the molecules return into their first state within an acceptable time by themselves i.e. by thermal excitation, or by the effect of the excitation signal 3. Otherwise, the switchback signal 17 is absolutely necessary.

Figure 7:
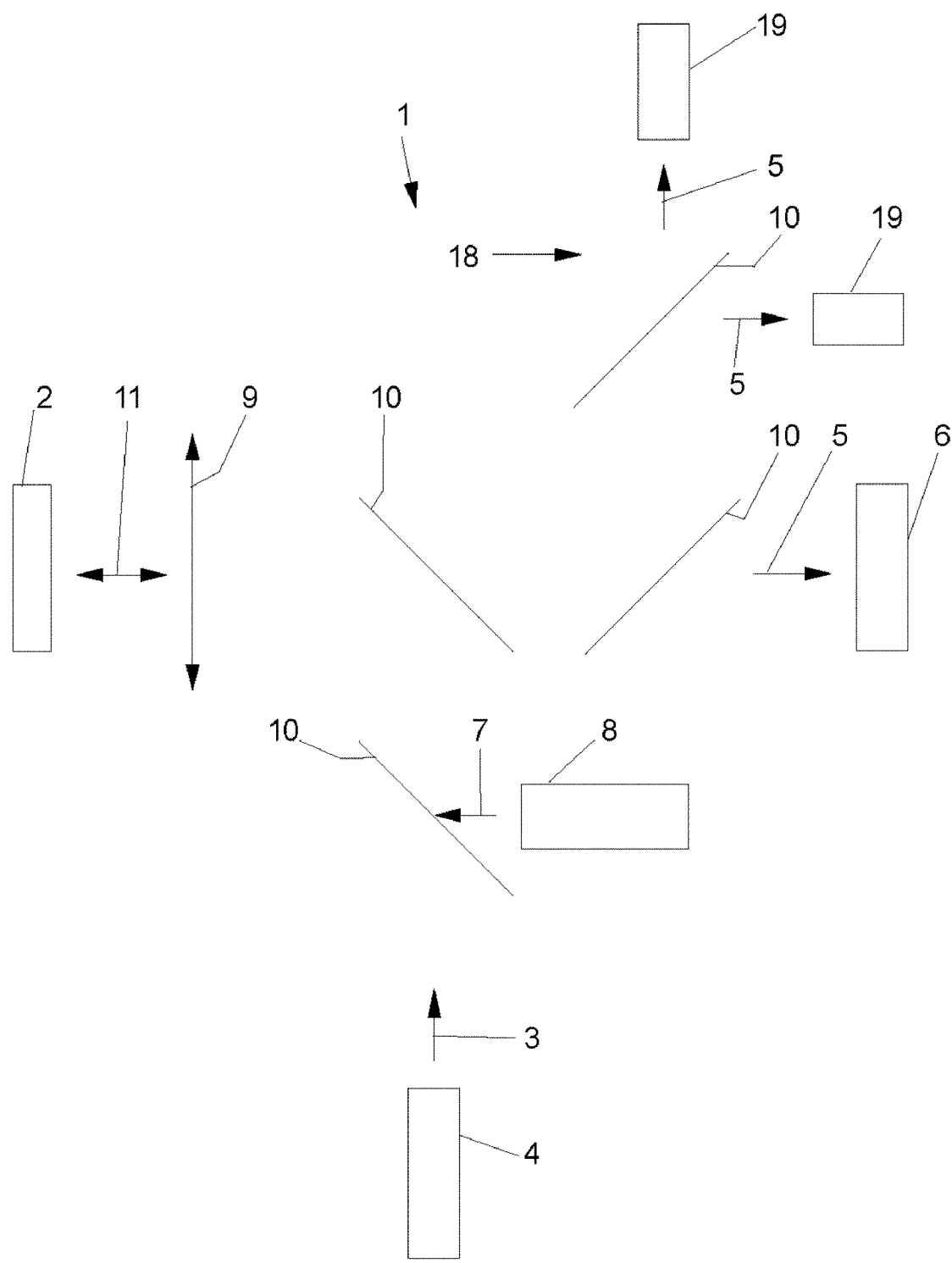
FIG. 7 schematically represents another embodiment of the fluorescent light microscope, here supplemented with a photodetector relative to FIG. 1.

The fluorescent light microscope 1 schematically represented in FIG. 7 does not comprise the supplementary switchback signal source 16 according to FIG. 6; it could however also be provided in this embodiment. FIG. 7, however, serves to explain the additional arrangement of a photodetector 18. The photodetector 18 is intended to register the chronological sequence of individual photons of the measurement signal 5, which come from a region of the specimen that corresponds to a plurality of pixels of the sensor array 6. This monitoring of the sequence of the photons is intended to be used to establish very rapidly whether only a single molecule is in the fluorescent state in the respective region, or whether a plurality of molecules are emitting fluorescent light from this region. If a plurality of molecules are involved, with a small size of the region this is an indication that the intensity distributions of the measurement light coming from it cannot be separated on the sensor array 6, i.e. cannot be used for determining the location of individual molecules. Accordingly, the registering of the measurement signal 5 by the sensor array 6 may be terminated in favor of a new selection of molecules with the switching signal 7. At least, readout of the corresponding regions of the sensor array 6 can be obviated. In this case, for example, it is expedient to provide photosensors 18 for various regions of the specimen 2 or the sensor array 6 in the form of a further array, but with a smaller number of pixels. Specifically, the photodetector 18 in FIG. 7 is designed as a coincidence detector arrangement, with two detector units 19 being connected in parallel with the aid of a semitransparent mirror 10 as a beam splitter. The coincidence detector arrangement detects those cases in which photons of the measurement light 15 strike both detector units 19 chronologically very close together, i.e. coincidences of photons.

Such coincidences cannot occur when there is a single fluorescent molecule in the region of the specimen 2 recorded by the photodetector 18, since a single fluorescent molecule can only ever emit a single photon owing to its excitation and emission of the next photon is only possible as a result of its next excitation, there being a minimum time between the individual excitations.

Figure 8:
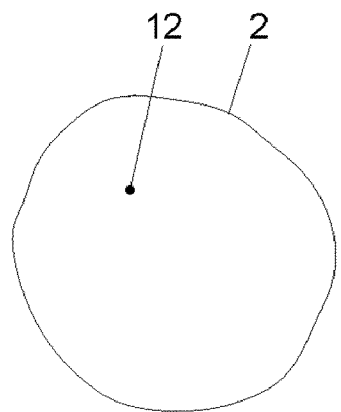
FIG. 8 shows a single molecule in the observation region of the photodetector according to FIG. 7.
Figure 9:
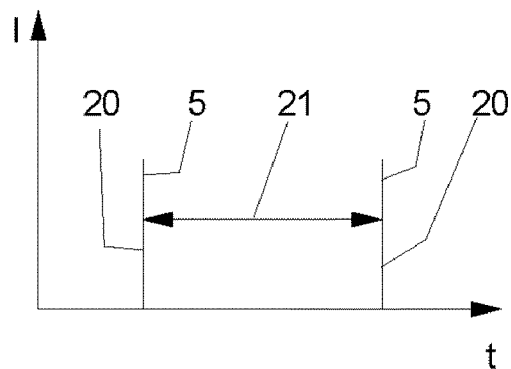
FIG. 9 schematically represents the chronological sequence of photons of the measurement signal, which the photodetector according to FIG. 7 receives from the molecule according to FIG. 8.
Figure 10:
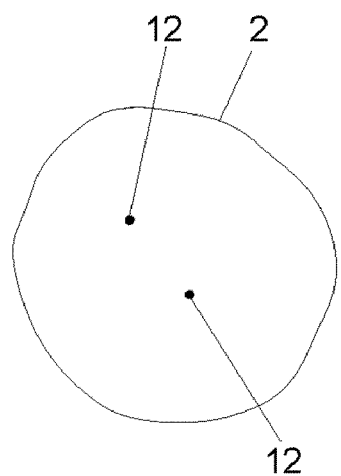
FIG. 10 schematically represents two molecules in the observation region of the photodetector according to FIG. 7.
Figure 11:
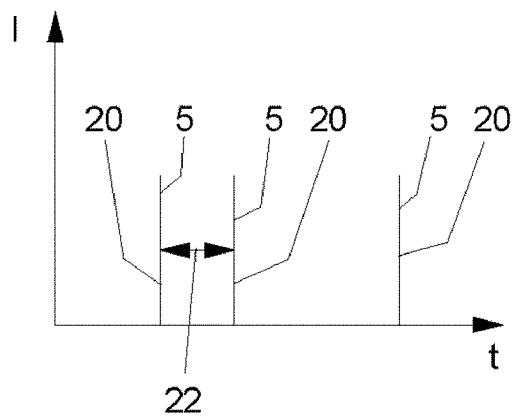
FIG. 11 schematically represents the sequence of photons of the measurement signal from the two molecules according to FIG. 10.

These relationships will be explained again with the aid of FIGS. 8 to 11. FIG. 8 shows a single molecule which according to FIG. 9 emits photons 20 of the measurement signal 5 that have a minimum time spacing 21. If however the photodetector 18 according to FIG. 7 registers a chronological sequence of photons 20 of the measurement signal 5, as schematically represented in FIG. 11 and in which a time spacing 22 that is very much smaller than the spacing 21 according to FIG. 9 occurs between two photons 20, this indicates at least two fluorescent molecules 12 in the region from which the measurement signal 5 is coming. This case is schematically represented in FIG. 10.

Figure 12:
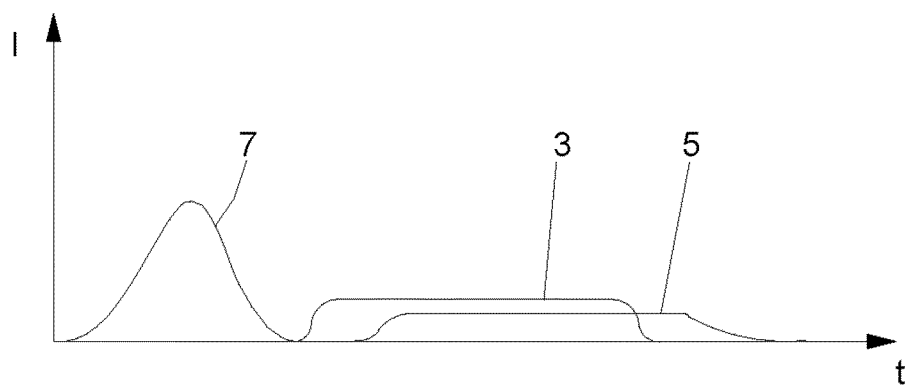
FIG. 12 schematically represents the chronological sequence of the various optical signals in the embodiment of the fluorescent light microscope according to FIG. 1.

FIG. 12 is a plot of the chronological sequence of the switching signal 7, the excitation signal 3 and the measurement signal 5 for the embodiment of the fluorescent light microscope according to FIG. 1. It is to be emphasized that the signal shapes are depicted only very schematically here and not necessarily corresponding to reality. The intention is essentially to show the chronological sequence with which particular molecules of the substance are initially converted into the second state by the switching signal 7, and are then excited into fluorescence by the excitation signal 3. This fluorescence leads to the measurement signal 5, which decays after the excitation signal 3 is extinguished. FIG. 12 schematically represents only a single cycle of the method carried out with the fluorescent light microscope 1. The next cycle begins with the same signal sequence, as soon as the molecules of the substance have returned from the second state into their first state by thermal excitation or owing to the excitation signal 3.

Figure 13:
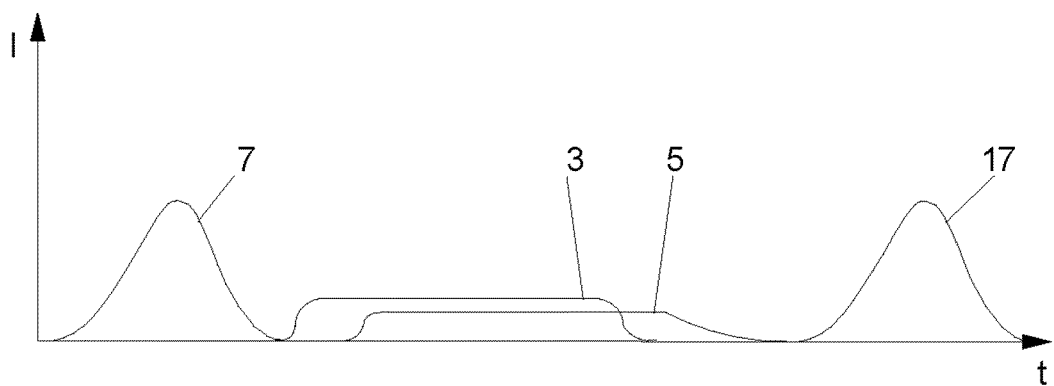
FIG. 13 schematically represents the chronological sequence of the various optical signals in the embodiment of the fluorescent light microscope according to FIG. 6.

In the signal sequence according to FIG. 13, which corresponds to the embodiment of the fluorescent light microscope 1 according to FIG. 6, the next cycle of the method with the next switching signal 7 can follow immediately, because the switchback signal 17 which returns the molecules of the substance in each case into their first state occurs at the end of every cycle.

Figure 14:
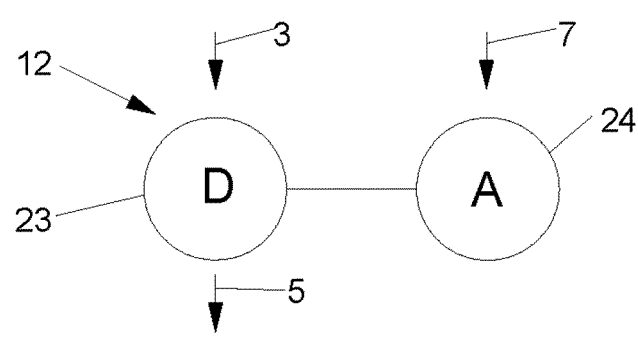
FIG. 14 schematically represents the structure and the function of a FRET pair comprising a donor and an acceptor, which may be used as a substance for marking the specimen's structure of interest in the new method.

FIG. 14 schematically represents a FRET pair comprising a donor 23 and an acceptor 24, which form subunits of a molecule 12. The donor 23 and the acceptor 24 could be proteins, which are fused to form the molecule 12. Specifically, the acceptor may be a protein known as Dronpa while the donor may be a protein of the ECFP type. The function of the FRET pair according to FIG. 14 in the new method is as follows. The acceptor 24 is a photochromic and changes its absorption spectrum owing to the switching signal 7. This shift of the absorption spectrum of the acceptor 24 leads to a change in the fluorescent behavior of the donor 23. Specifically, the donor 23 fluoresces since energy transfer from the donor to the acceptor due to excitation of the donor by the excitation signal 3 is no longer possible because of the change in the absorption spectrum of the acceptor 24, and deexcitation of the donor can now take place to an increased extent via the emission of fluorescent light i.e. the measurement signal 5.

Figure 15:
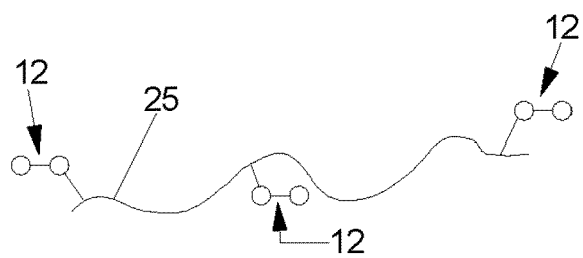
FIG. 15 schematically represents the marking of a single protein molecule with a plurality of FRET pairs according to FIG. 14.

FIG. 15 schematically represents the fact that a larger protein 25 may also be marked with a plurality of molecules 12 at a plurality of points, for example in order to observe conformational changes of the protein 25 such as foldings by the new method. The points at which the molecules 12, which are schematically represented in the form of a FRET pair according to FIG. 14, lie are typically closer together than a possible spatial resolution limit in the optical imaging of the protein 25. In the new method, however, only one of the molecules 12 on the protein 25 is ever converted into the fluoresceable state and then its location is exactly determined based on the measurement signal coming from it. This process is repeated many times with the selection of the respective molecule 12 whose location is determined exactly following statistical laws, so that with the limited number of molecules 12 on the protein 25 all the proteins 12 are interrogated after a few repetitions, even though the selection of each individual time is only determined by transition probabilities.

Figure 16:
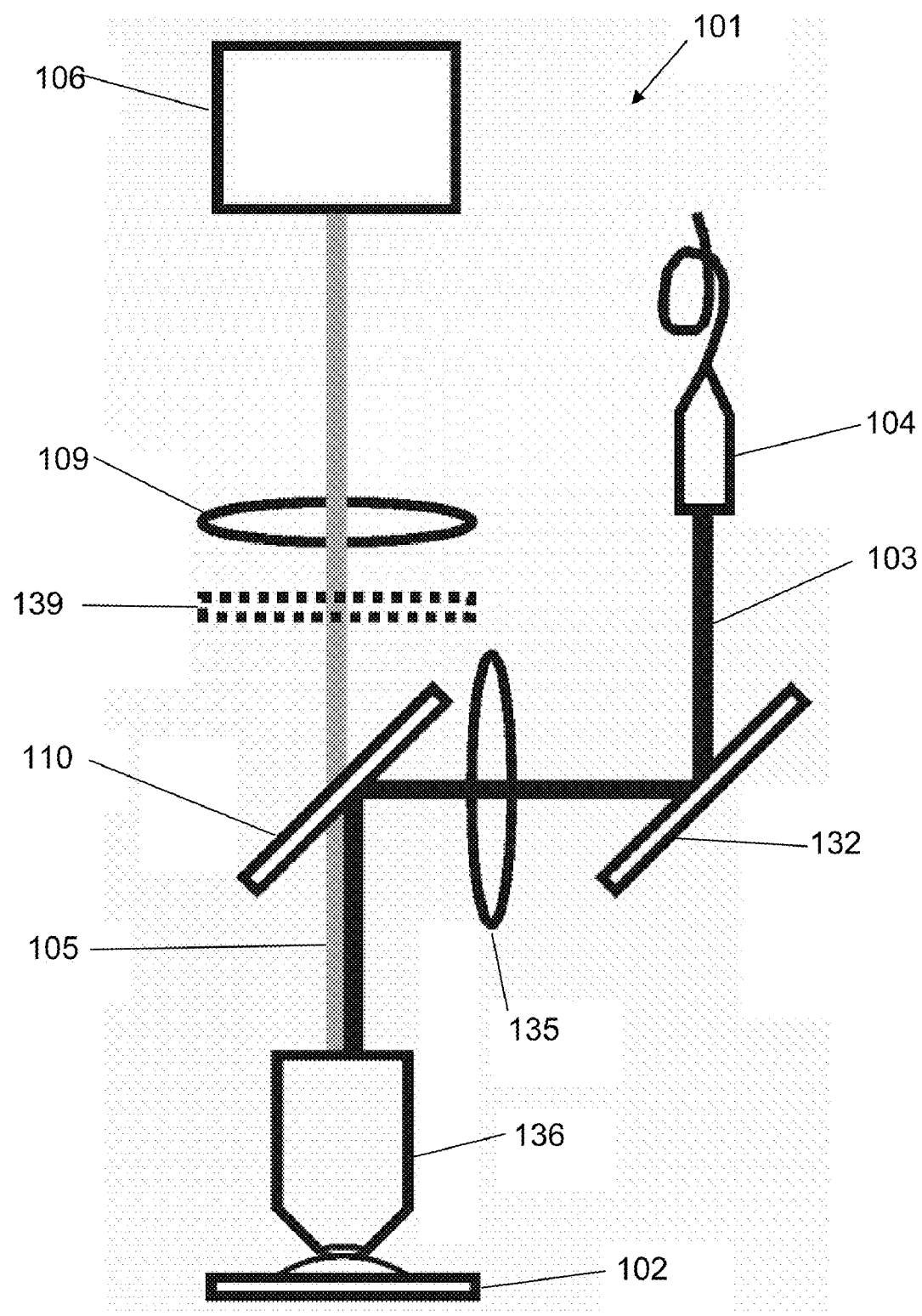
FIG. 16 shows the structure of a further fluorescent light microscope.
Figure 17:
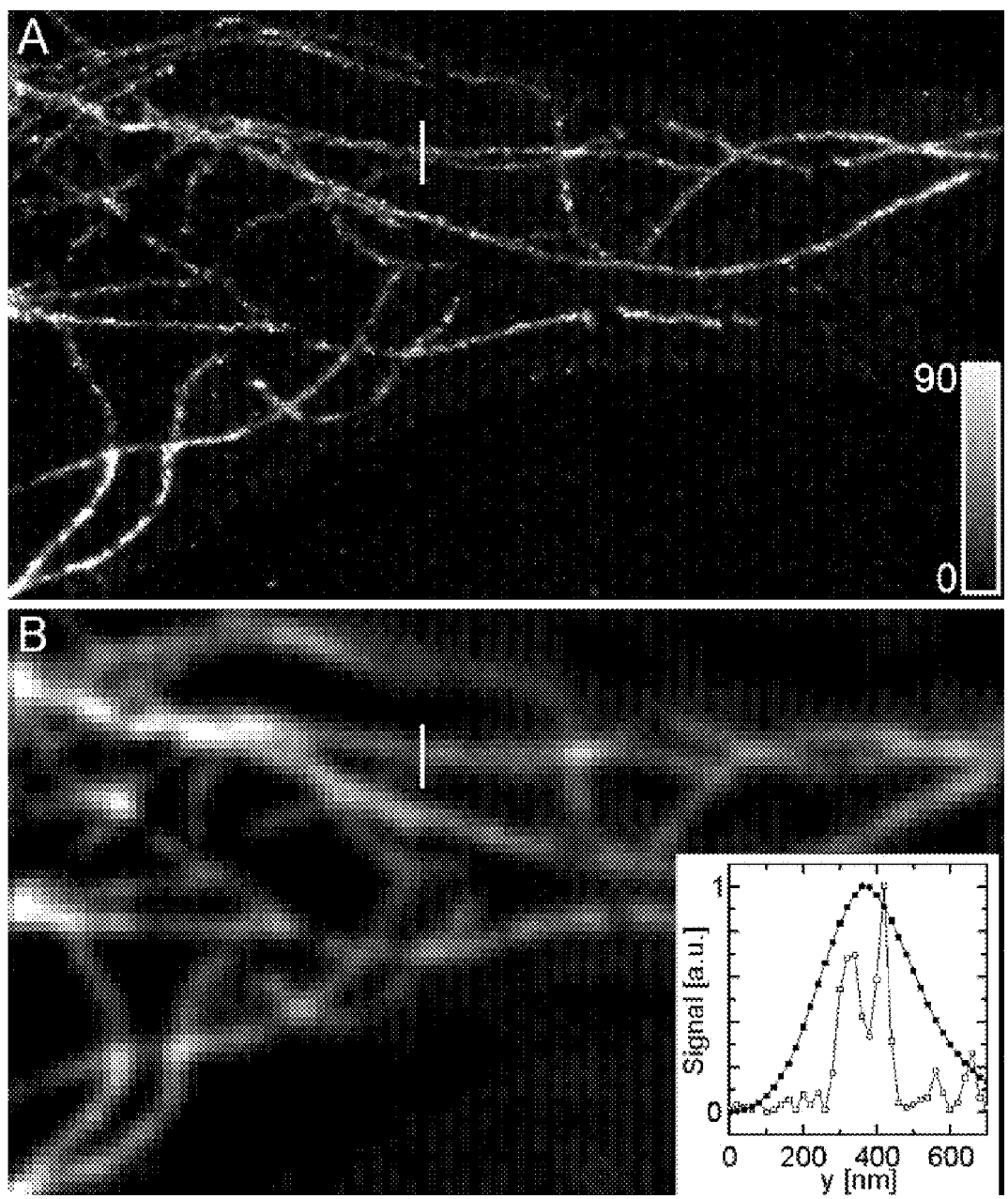
FIG. 17 (A) shows an overall image, recorded by the new method, of microtubuli of a PtK2 cell as the structure of interest. The structure is dyed with the dye rhodamine 6G. The medium, in which the cell is located, is an aqueous buffer solution with glucose oxidase and catalase (50 mM Tris, pH 7.5, 10 mM NaCl, glucose oxidase (Sigma, G2133), 40 µg/ml catalase (Roche Applied Science, 106810), 10% (w/v) glucose). The number of individual images recorded for the overall image is 61440 with exposure times of 5 ms. The light intensity was constant at 50 kW/cm$^2$.

When carrying out the method according to the invention for the high spatial resolution imaging of a structure of interest in a specimen 102 with the fluorescent light microscope 101 schematically represented in FIG. 16, light 103 on one wavelength (black line) from a light source 104 is provided via a mirror 132 and focused by means of the lens 135 into an objective 136. The light 103 is used for large-area illumination of the entire region of interest in the specimen 102. Fluorescent light 105 (gray line) from fluorescent dye in the specimen 102 is likewise collected by an objective, in this case the same objective 6, and separated from the light 103 by means of a dichroic mirror 110, and if necessary refined further by a suitable fluorescent light filter 139. In conjunction with the objective 135, a lens 109 ensures suitable imaging of the fluorescent molecules of the fluorescent dye onto a sensor array 106.

When carrying out a preferred embodiment of the method according to the invention using the fluorescent light microscope 101, the following steps are performed:

First, a structure of interest in a specimen is dyed with a non-switchable fluorescent dye.

The specimen is then embedded in a suitable environment. This may for example be PVA, or alternatively an aqueous medium (for example for living cells) from which oxygen is extracted. This measure is generally necessary since with modern technology and conventional fluorescent dyes, the lifetime of the dark triplets state in aqueous solutions without oxygen concentration reduction is not long enough to be able to separate individual molecule events. The oxygen reduction may for example be carried out by adding glucose oxidase and catalase. Such aqueous buffers are widely known media for microscopy. One medium, which is also suitable in principle for living cell applications, is:

88% (v/v) Gibco-DMEM (Invitrogen Corporation, Carlsbad, Calif.) with 10 mM HEPES, 10% (v/v) glucose oxidase (5 mg/ml, Sigma, G2133), 2% (v/v) catalase (2 mg/ml, Roche Applied Science, 106810).

Sometimes, when the marking density i.e. the spatial density of the fluorescent dye is too high, a sufficient fraction of the molecules of the fluorescent dye must be irreversibly bleached by suitable exposure of the specimen to the light before the start of the actual measurement. In any event, a sufficiently large fraction of the molecules must be pumped from their fluorescent first state into their dark second state by shining in the light before the start of the measurement, so that the images of the few molecules remaining in the fluorescent state on the sensor array lie further away from one another than the resolution limit on a sensor array. Typical intensities are between 1 and 100 $kW/cm^2$, depending on the environment and fluorescent dye. The intensity distribution of the fluorescent light, which can be recorded by the sensor array at the start of shining the light, shows the resolution-limited image of the structure of interest. This may subsequently be used as a reference for a termination criterion. In practice, for recording the resolution-limited image of the structure of interest, the exposure time must sometimes be adapted to a camera comprising the sensor array or the magnification thereof, or an intensity filter must be used since the camera will be optimized for the detection of individual molecule signals. As an alternative, a light signal of lower intensity may also be shone in order to record a diffraction-limited reference image, before the light signal which is used to convert the multiplicity of the molecules into the dark state.

The actual measurement can be started without delay once a sufficient fraction of the molecules has been pumped into the dark state, and in any event this must be done within a period of time which is much shorter than the lifetime of the dark state. The exposure time of the individual images is dictated by the average time over which a molecule, which is in the luminous first state, emits fluorescent light before it is converted back into the dark second state. In the examples used, this leads to a typical exposure time of from 2 to 10 ms. During this time, on average an order of magnitude of 1000 photons per molecule are recorded on the detector, before it is converted back into the dark state.

During the measurement, after molecules have been lost by irreversible bleaching, the intensity of the light may be reduced in order to achieve an optimal density of the molecules which are in the first state.

The duration of the entire measurement is dictated by the number of individual images and their exposure time. The number of individual images required is dictated by the selected termination criterion. For more complex structures, typically up to 100,000 images individual are recorded. The total recording time is therefore of the order of minutes.

We claim:

1. A method for high spatial resolution imaging of a structure of interest in a specimen, having the steps:
    selecting a substance from a group of substances which can be converted repeatedly by a switching signal from a first state into a second state, which can return from the second state into the first state, and which provide an optical measurement signal in one of their first and second states only;
    marking the specimen's structure of interest in the specimen with molecules of the substance;
    applying an intensity of the switching signal to the specimen in order to convert certain fractions of the substance into the second state by the switching signal, the intensity of the switching signal being set such that at least 10% of the molecules of the substance being in the one of the first and second states providing the optical measurement signal are at a distance from their closest neighboring molecules in the one of the first and second states providing the optical measurement signal, which is greater than the spatial resolution limit of the imaging of the specimen onto the sensor array;
    imaging the specimen onto a sensor array, a spatial resolution limit of the imaging being greater than an average distance between closest neighboring molecules of the substance in the specimen;
    using the sensor array to register the optical measurement signal which comes from the specimen, in order to record an intensity distribution of the measurement signal over the sensor array;
    separating the optical measurement signal which comes from molecules of the substance in the one of the first and second states providing the optical measurement signal, which are at a smaller distance from one another than the distance which is greater than the spatial resolution limit of the imaging of the specimen onto the sensor array, from the optical measurement signal which comes from the molecules of the substance in the one of the first and second states providing the optical measurement signal, which are at a distance from their closest neighboring molecules in the one of the first and second states providing the optical measurement signal, which is greater than the spatial resolution limit of the imaging of the specimen onto the sensor array; and
    determining the position in the specimen of the molecules of the substance from the intensity distribution of the measurement signal over the sensor array coming from the molecules of the substance in the one of the first and second states providing the optical measurement signal, which are at a distance from their closest neighboring molecules in the one of the first and second states providing the optical measurement signal, which is greater than the spatial resolution limit of the imaging of the specimen onto the sensor array, only.

2. The method as claimed in claim 1, wherein, in the step of separating, the intensity distribution of the measurement signal over the sensor array is checked for whether it corresponds to a single molecule or a plurality of molecules with regard to at least one of the following criteria aspects:
    total intensity of the measurement signal,
    shape of the intensity distribution of the measurement signal over the sensor array,
    area of the intensity distribution of the measurement signal over the sensor array.

3. The method as claimed in claim 2, wherein, in the step of applying, the intensity of the switching signal is adjusted such that at least 66% of the molecules of the substance being in the one of the first and second states providing the optical measurement signal are at a distance from their closest neighboring molecules in the one of the first and second states providing the optical measurement signal, which is greater than the spatial resolution limit of the imaging of the specimen onto the sensor array.

4. The method as claimed in claim 1, wherein the one of the first and second states providing the optical measurement signal is the first state.

5. The method as claimed in claim 1, wherein, in the step of applying, the intensity of the switching signal is adjusted such that at least 33% of the molecules of the substance being in the one of the first and second states providing the optical measurement signal are at a distance from their closest neighboring molecules in the one of the first and second states providing the optical measurement signal, which is greater than the spatial resolution limit of the imaging of the specimen onto the sensor array.

6. The method as claimed in claim 1, wherein, in the step of applying, the intensity of the switching signal is adjusted such that at least 90% of the molecules of the substance being in the one of the first and second states providing the optical measurement signal are at a distance from their closest neighboring molecules in the one of the first and second states providing the optical measurement signal, which is greater than the spatial resolution limit of the imaging of the specimen onto the sensor array.

7. The method as claimed in claim 1, wherein the intensity of the switching signal is set to a constant value over a region which has dimensions larger than the spatial resolution limit of the imaging of the specimen onto the sensor array.

8. The method as claimed in claim 7, wherein the constant value is established as a function of a local concentration of the substance in the specimen.

9. The method as claimed in claim 8, wherein the one of the first and second states providing the optical measurement signal is the first state, and wherein the local concentration of the substance in the specimen is determined when a larger fraction of the molecules of the substance are still in the first state.

10. The method as claimed in claim 7, wherein the local concentration of the substance in the specimen is determined when essentially all molecules of the substance are in the one of the first and second states providing the optical measurement signal.

11. The method as claimed in claim 1, wherein a region of the specimen which corresponds to a plurality of pixels of the sensor array is imaged onto a photodetector, in order to observe the chronological sequence of the emission of individual photons from the region.

12. The method as claimed in claim 1, wherein the substance is selected from a subgroup of substances which, in the one of the first and second states providing the optical measurement signal, can be excited by an optical excitation signal to spontaneously emit fluorescent light, which is registered as the optical measurement signal by the sensor array.

13. The method as claimed in claim 12, wherein the substance is a switchable fluorophore.

14. The method as claimed in claim 13, wherein the substance is selected from a subgroup of substances which can be converted from the second state back into the first state by an optical switchback signal.

15. The method as claimed in claim 1, wherein when marking the specimen's structure of interest with molecules of the substance, the molecules of the substance are expressed by gene technology together with protein molecules of the structure of interest in the specimen.

16. The method as claimed in claim 1, wherein, when marking the specimen's structure of interest with molecules of the substance, binding sites for molecules of the substance are expressed by gene technology together with protein molecules of the structure of interest in the specimen.

17. The method as claimed in claim 1, wherein a protein molecule in the specimen is marked at a plurality of different points with molecules of the substance.

18. The method as claimed in claim 1, wherein the steps are carried out in parallel with molecules of at least two different substances, which provide distinguishable optical measurement signals in one of their first and second states.

19. A method for high spatial resolution imaging of a structure of interest in a specimen, having the steps:
   selecting a substance from a group of substances,
      which have a first state with first fluorescent properties and a second state with second fluorescent properties;
      which can be excited by light of one wavelength to spontaneously emit fluorescent light;
      which can be converted from the first state into their second state by the light of the one wavelength and which can return from their second state into their first state;
   marking the specimen's structure of interest with molecules of the substance;
   imaging the specimen onto a sensor array, a spatial resolution limit of the imaging being greater than an average spacing between closest neighboring molecules of the substance in the specimen;
   exposing the specimen to the light of the one wavelength in a region which has dimensions larger than the spatial resolution limit of the imaging of the specimen onto the sensor array, at such an intensity that fractions of the molecules of the substance are being excited by the light of the one wavelength to spontaneously emit fluorescent light and being converted into their second state, and that at least 10% of the molecules of the substance belonging to the fraction of the molecules of the substance being excited by the light of the one wavelength to spontaneously emit fluorescent light are at a distance from their closest neighboring molecules belonging to the fraction of the molecules of the substance being excited by the light of the one wavelength to spontaneously emit fluorescent light, which is greater than the spatial resolution limit of the imaging of the specimen onto the sensor array;
   registering the fluorescent light which is spontaneously emitted out of the region by varying fractions of the molecules of the substance being excited by the light of the one wavelength to spontaneously emit fluorescent light, in a plurality of images recorded by the sensor array during continued exposure of the region to the light of the one wavelength; and
   separating the fluorescent light which comes from molecules of the substance being excited by the light of the one wavelength to spontaneously emit fluorescent light, which are at a smaller distance from one another than the distance which is greater than the spatial resolution limit of the imaging of the specimen onto the sensor array, from the optical measurement signal which comes from the molecules of the substance being excited by the light of the one wavelength to spontaneously emit fluorescent light, which are at a distance from their closest neighboring molecules being excited by the light of the one wavelength to spontaneously emit fluorescent light, which is greater than the spatial resolution limit of the imaging of the specimen onto the sensor array; and
   determining the position in the specimen of the molecules of the substance from the fluorescent light recorded by the sensor array coming from the molecules of the substance being excited by the light of the one wavelength to spontaneously emit fluorescent light, which are at a distance from their closest neighboring molecules being excited by the light of the one wavelength to spontaneously emit fluorescent light, which is greater than the spatial resolution limit of the imaging of the specimen onto the sensor array, only.

20. The method as claimed in claim 19, wherein, in the step of separating, the fluorescent light is checked for whether it corresponds to a single molecule or a plurality of molecules with regard to at least one of the following criteria aspects:
   total intensity of the fluorescent light,
   shape of the intensity distribution of the fluorescent light over the sensor array,
   area of the intensity distribution of the fluorescent light over the sensor array.

21. The method as claimed in claim 19, wherein at the beginning of the exposure of the specimen to the light of the one wavelength, its intensity is set such that the substance is converted into its second state, until more than 90% of the molecules of the substance have been converted into the second state.

22. The method as claimed in claim 21, wherein the first state and the second state are different electronic states of the molecules of the substance.

23. The method as claimed in claim 22, wherein the substance is not a switchable fluorophore.

24. The method as claimed in claim 22, wherein the first state is a singlet state and the second state is a triplet state of the molecules of the substance.

25. The method as claimed in claim 22, wherein at least one measure is implemented which modifies the lifetime of the second state of the molecules of the substance in the specimen.

26. The method as claimed in claim 22, wherein at least one measure is implemented which extends the lifetime of the second state of the molecules of the substance in the specimen.

27. The method as claimed in claim 22, wherein before the images are recorded, a fraction of the substance is converted by photobleaching by means of a high intensity of light, which is selected from the light of the one wavelength and the light of another wavelength, into a persistent dark state which differs from the first state and the second state.

28. The method as claimed in claim 19, wherein at the start of the exposure of the specimen to the light of the one wavelength, its intensity is set such that the substance is converted into its second state until essentially all of the molecules of the substance have been converted into the second electronic state.

29. The method as claimed in claim 19, wherein the substance is selected from a subgroup of substances which comprises
    substances that return spontaneously from their second state into their first state;
    substances that return from their second state into their first state by the action of the light of the one wavelength; and
    substances that return into their first state spontaneously as well as by action of the light of the one wavelength.

30. The method as claimed in claim 19, wherein the intensity of the light of the one wavelength is set to a constant value during the recording of the images.

31. The method as claimed in claim 19, wherein the intensity of the light of the one wavelength is set to an intensity profile, time-modulated with the sequence of the recording of the images, during the recording of the images.

32. The method as claimed in claim 19, wherein the light of the one wavelength is directed onto the region of the specimen as a continuous wave.

33. The method as claimed in claim 19, wherein the light of the one wavelength is directed onto the region of the specimen in rapid pulses which are not temporally resolved during the recording of the images.

34. The method as claimed in claim 19, wherein the individual recorded images are evaluated online in respect of the maximum density at which they show separable molecules of the substance being excited by the light of the one wavelength to spontaneously emit fluorescent light, and in that the intensity of the light is varied until a density threshold for such separable molecules of the substance being excited by the light of the one wavelength to spontaneously emit fluorescent light is reached.

35. The method as claimed in claim 34, wherein a termination criterion for the recording of further images of the same region of the specimen is defined on the basis of the intensity distribution of the fluorescent light of the entire substance in the specimen.

36. The method as claimed in claim 19, wherein, at the start of exposing the specimen to the light of the one wavelength, an intensity distribution of the fluorescent light of the entire substance in the specimen is recorded by the sensor array with the spatial resolution of the imaging of the specimen onto the sensor array.

37. The method as claimed in claim 36, wherein each position of a molecule of the substance registered in the mutually successive images convoluted with the PSF (Point Spread Function) of the imaging of the specimen onto the sensor array, and this reconstruction is compared with the initially recorded intensity distribution.

38. The method as claimed in claim 19, wherein the structure of interest of the specimen is marked with the substance by modifying a biological specimen with gene technology so that it itself expresses the substance.

39. The method as claimed in claim 19, wherein the structure of interest of the specimen is marked with the substance by modifying a biological specimen with gene technology so that it expresses proteins with specific binding sites for the substance.

40. The method as claimed in claim 19, wherein the structure of interest of the specimen is marked with the substance by modifying a biological specimen with gene technology so that it expresses proteins with specific binding sites for a linker coupled to the substance.

* * * * *